(12) United States Patent
Oglaza et al.

(10) Patent No.: US 8,986,386 B2
(45) Date of Patent: Mar. 24, 2015

(54) APPARATUS FOR BONE RESTORATION OF THE SPINE AND METHODS OF USE

(75) Inventors: Jean-François Oglaza, Balma (FR); Ezzine Banouskou, Toulouse (FR); Cécile Vienney, Belin-Beliet (FR)

(73) Assignee: Vexim SAS, Balma (FR)

( * ) Notice: Subject to any disclaimer, the term of this patent is extended or adjusted under 35 U.S.C. 154(b) by 372 days.

(21) Appl. No.: 13/256,090

(22) PCT Filed: Mar. 12, 2009

(86) PCT No.: PCT/IB2009/005385
§ 371 (c)(1),
(2), (4) Date: Nov. 22, 2011

(87) PCT Pub. No.: WO2010/103344
PCT Pub. Date: Sep. 16, 2010

(65) Prior Publication Data
US 2012/0071977 A1    Mar. 22, 2012

(51) Int. Cl.
*A61F 2/44*       (2006.01)
*A61B 17/70*     (2006.01)
(Continued)

(52) U.S. Cl.
CPC ......... *A61B 17/7065* (2013.01); *A61B 17/8858* (2013.01); *A61F 2/442* (2013.01); *A61F 2/4611* (2013.01); *A61B 2017/0256* (2013.01); *A61F 2/441* (2013.01); *A61F 2/4455* (2013.01); *A61F 2002/30235* (2013.01); *A61F 2002/30579* (2013.01); *A61F 2002/30581* (2013.01); *A61F 2002/30594* (2013.01); *A61F 2002/30624* (2013.01); *A61F 2002/3097* (2013.01); *A61F 2230/0069* (2013.01); *A61F 2310/00023* (2013.01)

USPC ........................... 623/17.15; 606/90; 606/105

(58) Field of Classification Search
USPC ............. 623/17.11, 17.15, 17.16; 606/92–94, 606/105
See application file for complete search history.

(56) References Cited

U.S. PATENT DOCUMENTS 4,796,612 A * 1/1989 Reese ........................... 606/324
4,932,975 A    6/1990 Main et al.
(Continued)

FOREIGN PATENT DOCUMENTS

CN          1162349 A    10/1997
WO     WO-0101895 A1    1/2001
(Continued)

OTHER PUBLICATIONS

International Search Report for PCT No. PCT/IB2009/005385.
(Continued)

*Primary Examiner* — Andrew Yang
(74) *Attorney, Agent, or Firm* — Cooley LLP; Brian P. Hopkins

(57) ABSTRACT

The subject disclosure is directed to systems, apparatuses, devices and methods for vertebral and spinal correction. In some embodiments, an expandable implant is provided which may be inserted inside the vertebral body and/or between two vertebrae, for instance, for maintenance and/or restoration of a space therein or there between. In certain embodiments, the implant includes a mechanical resistance that prevents the expandable implant from contracting once it has been expanded. Methods of treatment and methods of use of such implants for the alleviation of back pain (for example) are also provided herein.

40 Claims, 20 Drawing Sheets

(51) Int. Cl.
   *A61B 17/88* (2006.01)
   *A61F 2/46* (2006.01)
   *A61B 17/02* (2006.01)
   *A61F 2/30* (2006.01)

(56) References Cited

U.S. PATENT DOCUMENTS

| | | | |
|---|---|---|---|
| 4,961,740 A | 10/1990 | Ray et al. | |
| 4,969,888 A | 11/1990 | Scholten et al. | |
| 5,059,193 A * | 10/1991 | Kuslich | 606/247 |
| 5,108,404 A | 4/1992 | Scholten et al. | |
| 5,665,122 A | 9/1997 | Kambin | |
| 5,693,100 A | 12/1997 | Pisharodi | |
| 5,695,515 A | 12/1997 | Orejola | |
| 5,720,746 A | 2/1998 | Soubeiran | |
| 5,908,448 A | 6/1999 | Roberts et al. | |
| 5,972,015 A | 10/1999 | Scribner et al. | |
| 5,980,522 A | 11/1999 | Koros et al. | |
| 6,039,761 A | 3/2000 | Li et al. | |
| 6,066,154 A | 5/2000 | Reiley et al. | |
| 6,102,950 A | 8/2000 | Vaccaro | |
| 6,126,689 A | 10/2000 | Brett | |
| 6,127,597 A | 10/2000 | Beyar et al. | |
| 6,176,882 B1 | 1/2001 | Biedermann et al. | |
| 6,193,757 B1 | 2/2001 | Foley et al. | |
| 6,214,050 B1 | 4/2001 | Huene | |
| 6,235,043 B1 | 5/2001 | Reiley et al. | |
| 6,248,110 B1 | 6/2001 | Reiley et al. | |
| 6,261,289 B1 | 7/2001 | Levy | |
| 6,280,456 B1 | 8/2001 | Scribner et al. | |
| 6,332,895 B1 | 12/2001 | Suddaby | |
| 6,395,031 B1 | 5/2002 | Foley et al. | |
| 6,423,083 B2 | 7/2002 | Reiley et al. | |
| 6,454,807 B1 | 9/2002 | Jackson | |
| 6,488,710 B2 | 12/2002 | Besselink | |
| 6,554,833 B2 | 4/2003 | Levy et al. | |
| 6,582,431 B1 | 6/2003 | Ray | |
| 6,595,998 B2 | 7/2003 | Johnson et al. | |
| 6,607,544 B1 | 8/2003 | Boucher et al. | |
| 6,623,505 B2 | 9/2003 | Scribner et al. | |
| 6,632,235 B2 | 10/2003 | Weikel et al. | |
| 6,663,647 B2 | 12/2003 | Reiley et al. | |
| 6,664,897 B2 | 12/2003 | Pape et al. | |
| 6,676,665 B2 | 1/2004 | Foley et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,740,093 B2 | 5/2004 | Hochschuler et al. | |
| 6,783,530 B1 | 8/2004 | Levy | |
| 6,929,647 B2 | 8/2005 | Cohen | |
| 6,953,477 B2 | 10/2005 | Berry | |
| 6,979,341 B2 | 12/2005 | Scribner et al. | |
| 6,981,981 B2 | 1/2006 | Reiley et al. | |
| 7,044,954 B2 | 5/2006 | Reiley et al. | |
| 7,070,598 B2 | 7/2006 | Lim et al. | |
| 7,087,055 B2 | 8/2006 | Lim et al. | |
| 7,153,306 B2 | 12/2006 | Ralph et al. | |
| 7,217,293 B2 | 5/2007 | Branch, Jr. | |
| 7,234,468 B2 | 6/2007 | Johnson et al. | |
| 7,241,303 B2 | 7/2007 | Reiss et al. | |
| 7,261,720 B2 | 8/2007 | Stevens et al. | |
| 7,264,622 B2 | 9/2007 | Michelson | |
| 7,318,839 B2 | 1/2008 | Malberg et al. | |
| 7,621,950 B1 | 11/2009 | Globerman et al. | |
| 7,763,028 B2 | 7/2010 | Lim et al. | |
| 7,799,080 B2 | 9/2010 | Doty | |
| 7,846,206 B2 | 12/2010 | Oglaza et al. | |
| 7,879,104 B2 | 2/2011 | Dewey et al. | |
| 8,328,818 B1 * | 12/2012 | Seifert et al. | 606/105 |
| 2001/0032020 A1 | 10/2001 | Besselink | |
| 2002/0065548 A1 | 5/2002 | Birdsall et al. | |
| 2002/0120327 A1 | 8/2002 | Cox et al. | |
| 2002/0151976 A1 | 10/2002 | Foley et al. | |
| 2003/0065396 A1 | 4/2003 | Michelson | |
| 2003/0074064 A1 | 4/2003 | Gerbec et al. | |
| 2003/0171812 A1 | 9/2003 | Grunberg et al. | |
| 2003/0220650 A1 | 11/2003 | Major et al. | |
| 2003/0236520 A1 | 12/2003 | Lim et al. | |
| 2004/0073308 A1 | 4/2004 | Kuslich et al. | |
| 2004/0087947 A1 | 5/2004 | Lim et al. | |
| 2004/0102774 A1 | 5/2004 | Trieu | |
| 2004/0167625 A1 | 8/2004 | Beyar et al. | |
| 2004/0210231 A1 | 10/2004 | Boucher et al. | |
| 2004/0215343 A1 | 10/2004 | Hochschuler et al. | |
| 2005/0143827 A1 | 6/2005 | Globerman et al. | |
| 2005/0182416 A1 | 8/2005 | Lim et al. | |
| 2005/0228391 A1 | 10/2005 | Levy et al. | |
| 2005/0273135 A1 | 12/2005 | Chanduszko et al. | |
| 2006/0004455 A1 | 1/2006 | Leonard et al. | |
| 2006/0085070 A1 * | 4/2006 | Kim | 623/17.11 |
| 2006/0149379 A1 | 7/2006 | Kuslich et al. | |
| 2006/0271049 A1 | 11/2006 | Zucherman et al. | |
| 2007/0016303 A1 | 1/2007 | Jackson | |
| 2007/0021836 A1 | 1/2007 | Doty | |
| 2007/0032790 A1 | 2/2007 | Aschmann et al. | |
| 2007/0032791 A1 | 2/2007 | Greenhalgh | |
| 2007/0142915 A1 | 6/2007 | Altarac et al. | |
| 2007/0173826 A1 | 7/2007 | Canaveral et al. | |
| 2007/0260315 A1 | 11/2007 | Foley et al. | |
| 2008/0065087 A1 | 3/2008 | Osorio et al. | |
| 2008/0065089 A1 | 3/2008 | Osorio et al. | |
| 2008/0086133 A1 | 4/2008 | Kuslich et al. | |
| 2008/0114367 A1 | 5/2008 | Meyer | |
| 2008/0125784 A1 | 5/2008 | Rabiner et al. | |
| 2008/0140079 A1 | 6/2008 | Osorio et al. | |
| 2008/0140207 A1 | 6/2008 | Olmos et al. | |
| 2008/0147193 A1 | 6/2008 | Matthis et al. | |
| 2008/0183204 A1 | 7/2008 | Greenhalgh et al. | |

FOREIGN PATENT DOCUMENTS

| | | |
|---|---|---|
| WO | WO-0154598 A1 | 8/2001 |
| WO | WO-0166047 A1 | 9/2001 |
| WO | WO-2003003951 A1 | 1/2003 |
| WO | WO-2004026188 A2 | 4/2004 |
| WO | WO-2004034924 A2 | 4/2004 |
| WO | WO-2004047689 A1 | 6/2004 |
| WO | WO-2004086934 A2 | 10/2004 |
| WO | WO 2005/120400 A2 | 12/2005 |
| WO | WO-2006068682 A1 | 6/2006 |
| WO | WO-2006116760 A2 | 11/2006 |
| WO | WO-2007041665 A2 | 4/2007 |
| WO | WO-2007073488 A2 | 6/2007 |
| WO | WO-2007076308 A2 | 7/2007 |
| WO | WO-2007076374 A2 | 7/2007 |
| WO | WO-2007076376 A2 | 7/2007 |
| WO | WO-2007084239 A2 | 7/2007 |

OTHER PUBLICATIONS

International Search Report and Written Opinion of the International Searching Authority corresponding to International Application PCT/IB2005/002631 date of mailing Feb. 7, 2006.

French Preliminary Search Report corresponding to French Patent Application No. 04 06211 dated Feb. 15, 2005.

French Preliminary Search Report corresponding to French Patent Application No. 05 05798 dated Oct. 28, 2005.

International Preliminary Report on Patentability, issued Sep. 13, 2011 for PCT/IB2009/005385, filed Mar. 12, 2009.

* cited by examiner

APPARATUS FOR BONE RESTORATION OF THE SPINE AND METHODS OF USE

FIELD OF THE DISCLOSURE

Embodiments of the present disclosure are directed to spinal implants, and more particularly, to intervertebral and intravertebral implants.

BACKGROUND OF THE DISCLOSURE

The spinal column is made up of four main components: the spinal chord, the vertebra, the ligaments, and the intervertebral disc, and each may play a role in back pain. Generally, back pain may be caused by spinal instability, disc or ligament degeneration, bone joint dislocation, spinal root or articulation compression, and the like. For instance, deterioration of the intervertebral disc, such as a result of spinal stenosis, can lead to extreme discomfort and pain.

Accordingly, a common source of back pain is the result of the degeneration or herniation of the intervertebral disc, causing compression of the spinal column, which in turn can lead to the pinching of the spinal nerves and the release of inflammatory chemical mediators that promote swelling and inflammation thereby further irritating spinal nerves.

One method used for the relief of back pain, such as that caused by spinal stenosis, involves surgery designed to remove and/or reduce pressure on the spinal nerves/roots caused by such mechanical breakdown of the spinal column. Several techniques, such as interspinous process decompression, are known for effecting a vertebral correction, e.g., to attempt to restore an intervertebral space to its original shape or distance.

For instance, where back pain is caused by deterioration of the intervertebral disc, intervertebral implants, such as cages or disc prosthesis, have been designed to be inserted into the deteriorated region between two vertebral endplates in an effort to stabilize or increase the space between the vertebrae. Such intervertebral implants, however, limit the extent to which vertebrae can move towards each other since, when the spine is extended, spinous processes tend to come into abutment against the surfaces of the implants. Furthermore, since implants do not have the same mechanical properties as that of an intervertebral disc, the overall mechanical properties of the spine present significant discontinuities compared with an intact spine, thereby increasing deterioration of the intervertebral disc.

Accordingly, there is a need in the art for a spinal implant and corresponding associated methods (e.g. method of use) that reduce the above noted disadvantages of implants that are used to address spinal complications, and provide for the reduction of back pain as well as the restoration of the spine. At least some of the embodiments of the present disclosure meet these and other needs in the art.

SUMMARY OF THE DISCLOSURE

Some of the embodiments of the subject disclosure are directed toward an expansible/expandable implant (expansible and expandable being used interchangeably in the present disclosure). The implant may be inserted between two portions of a vertebra, or within an intervertebral space between two vertebrae, for the restoration of the spine (for example). For instance, in some embodiments, the implant may be used to restore and/or expand the distance between two vertebrae (e.g., between two adjacent vertebrae). In some embodiments, the implant may be used as a vertebroplasty device to treat a compression fracture(s) of a vertebral body.

Some embodiments of the subject disclosure are directed toward a vertebral expandable implant which comprises first and second bearing surfaces intended to move away from one another during expansion of the implant, at least first and second opposed ends associated with each of the bearing surfaces, and a retaining member for retaining the implant in an expanded configuration. The retaining element comprises a first end associated with the first end of the implant and a second end associated with the second end of the implant. A first engagement element provided proximate the second end of the retaining element for engagement with a second engagement element provided on the second end of the implant, where engagement between the first and second engagement element substantially prevents the second end of the implant from moving away from the first end of the implant.

In some such embodiments, the first engagement element may comprise one or more protruding ridges that extend outward away from the outer surface of the retaining member, and the second engagement element may comprise one or more recesses that extend inward away from the outer surface of the end of the implant, wherein upon expansion of the implant, at least a portion of at least one of the ridges abuts a portion of and/or is received by at least a portion of one or more recesses.

In some such embodiments, the second engagement element may comprise one or more protruding ridges that extend outward away from the outer surface of the end of the implant, and the first engagement element may comprise one or more recesses that extend inward away from the outer surface of the retaining element. Upon expansion of the implant, at least a portion of at least one of the ridges abuts a portion of and/or is received by at least a portion of one or more recesses.

In some embodiments, an intervertebral expandable implant is presented. In some embodiments, an intravertebral expandable implant is presented. For instance, in certain embodiments, an intervertebral expandable implant is provided, wherein the implant is configured for being positioned between two separate vertebral bodies, such as between the spinous process of two vertebral bodies; and in certain embodiments, an intravertebral expandable implant is provided, wherein the implant is configured for being positioned within a vertebral body, such as for the purpose of restoring the space therein. Accordingly, in some embodiments, an intervertebral and/or intravertebral implant is presented wherein the implant comprises first and second bearing surfaces, where the first and second surfaces are intended to move away from one another during expansion of the implant, at least first and second opposed end members associated with each of the bearing surfaces, a retaining element and at least a pair of supports associated with at least one of the bearing surfaces. At least one of the bearing surfaces additionally associated with at least one of the end members, where a first support of the pair includes a first engagement element, and a second support of the pair includes a second engagement element. Upon expanding the implant a predetermined amount, at least a portion of the first engagement element engages with at least a portion of the second engagement element to prevent movement of the end members toward one another.

In some embodiments, a method for restoring an intervertebral space between two vertebral bones, is presented, and comprises the steps of inserting an expandable implant between two vertebrae, where the expandable implant includes a contracted and an expanded configuration. The implant may comprise any of the previously disclosed implant embodiments described throughout this disclosure. The method also includes positioning the implant between the vertebrae and expanding the implant from the contracted configuration to the expanded configuration and thereby restoring the intervertebral space.

In some embodiments, a method for restoring an intravertebral space within a vertebral body, is presented, and comprises the steps of inserting an expandable implant into a space within a vertebra, where the expandable implant includes a contracted and an expanded configuration. The implant may comprise any of the previously disclosed implant embodiments described throughout this disclosure. The method also includes positioning the implant within the vertebra and expanding the implant from the contracted configuration to the expanded configuration and thereby restoring the intravertebral space.

Accordingly, in some embodiments, a method for restoring a space, for instance the space between two vertebrae or the space between two surfaces within a vertebra, is provided. The method may include one or more of the following steps. For example, the method may include accessing the space, inserting an implantable expandable device of the disclosure therein, e.g., in a collapsed configuration, positioning the expandable device between two surfaces within the space, and expanding the device so as to restore the space. The step of accessing the step may include one or more of surgically creating an entry through the tissue of a patient, inserting a trocar there through, associating a pin with the trocar, sliding an awl over the pin, applying a drill and/or tube guide, e.g., wire, over the pin, shaping the space via employment of the drill, insert an implant gauge to prepare the space, associate the implant with the implant holder and insert the implant and holder through the trocar to the site of delivery, and expanding the implant along a plane of expansion. One, two, or more expandable implants may be delivered in this manner. Once the one or more implants have been delivered and expanded, the implant holder may be removed and an injection tube may be inserted through the trocar, and cement may be injected into the space. The injection tube and/or trocar may be removed along with any other instrumentation and the access may be closed using routine surgical procedures.

In some embodiments, an implant is presented that includes a single plane of expansion intrinsic to the implant, for instance, a plane of expansion that corresponds to a plane between a two vertebrae or a plane of bone restoration.

Some embodiments of the implant may further include at least one top (or bottom) plate (or other element/member to bear against bone or other tissue), and preferably, first and second opposed plates (i.e., top and bottom), or other bearing element/member having a bearing surface to bear against bone or other tissue, that are intended to move away from one another according to a plane of expansion (for example) as the implant is expanded. The opposed plates may include corresponding first and second bearing surfaces, respectively, one or both of which may bear against a bone surface during use. In certain embodiments, the first and second bearing surfaces may include (or at least one of such surfaces may further include) a recess configured for engaging a portion of one of two surfaces of a bone or a portion thereof. In certain embodiments, the first and second bearing surfaces do not include a recess, but rather a substantially flat portion of the bearing surfaces engage a portion of one of two surfaces of a bone or a portion thereof.

Some embodiments of the disclosed implant may additionally include at least first and second opposed end members that are associated with each of the opposed plates (either directly or through other structural members). In some embodiments, the disclosed implant includes an extended retaining element, which retaining element is configured for being associated with the first and second opposed end members.

For example, in certain embodiments, the first and second opposed end members may include a distal end member and a proximal end member, wherein the opposed end members are separated from one another by a distance d. In certain embodiments, at least one of the end members, e.g., the distal end member, includes an aperture configured for receiving at least a portion of the extended retaining element, and the other end member, e.g., the proximal end member, includes an abutment configured for receiving an end portion of the extended retaining element, once the extended element has been inserted through the aperture of the distal end member. In certain instances, the distal end member may be moveably associated with the extended retaining element such that the first, e.g., distal, end member may be capable of moving horizontally along the extended retaining member toward the second, e.g., proximal, end member thereby shortening the distance d between the two end members. In certain embodiments, as the first end member moves along the extended retaining element, toward the second end member, the implant is expanded.

In certain embodiments, the retaining element/member includes a raised ridge or a notch portion which interlocks with another corresponding member of the implant. In certain instances, the retaining member and at least one of the end members are configured for interacting in such a manner that as the implant is expanded, at least a portion of the end member becomes associated with the retaining member, which association prevents the implant from contracting once expanded.

Accordingly, in certain embodiments, as a first, e.g., distal, end member moves along the extended retaining element, and the implant is expanded and the end member, or a portion thereof, contacts and/or locks to a retaining member, or a portion thereof, and is thus prevented from moving away (e.g., horizontally) from the opposed, e.g., proximal, end member. In this manner, the retaining member is adapted for retaining the implant, once expanded, in the expanded configuration, and thus, the retaining member prevents the implant from contracting once expanded. Such "retaining" therefore may also be locking, that is, locking the implant in an expanded configuration.

In some embodiments, the disclosed implant may include an extended retaining element, however, the retaining element does not include ridges/notches (e.g., does not include engagement elements). Rather, the expansible implant may include at least one or more supports for one or more of the plates and/or bearing surfaces. For instance, the expansible implant may include a pair of first and second supports that are associated with at least one of the first and second plates and may additionally be associated with at least one of the first and second end members.

In certain instances, at least one of the pair of the first and second supports includes an engagement element and an engagement element receiving member. For example, at least one of the first and second supports may include the engagement element and another of the first and second supports may include the engagement element receiving member. In certain instances, the engagement element and the receiving member may be configured for associating with one another in such a manner so as to restrain the implant from contracting once expanded.

For instance, in certain embodiments, the expansible implant includes a pair of first and a second supports wherein one of the pair of first and second supports connect one of the opposed plates with one of the opposed end members (e.g., a distal end member), and the other of the pair of first and second supports connect another of the opposed plates with another of the opposed end members (e.g., a proximal end member). In such an instance, the end members, supports, opposed plates, and retaining element, are configured such that as one of the end members, e.g., the distal end member, moves along the retaining element toward the proximal end member, the supports move axially away from the retaining element thereby pushing the opposed plates outwards and away from one another. Where at least one of the first and second supports include an engagement element and the other of the first and second supports includes an engagement element receiving member, as the implant is expanded, the engagement element on a first support becomes associated with an engagement element receiving member on a corresponding second support, which association functions to restrain the implant from contracting once expanded.

Methods of using at least some of the disclosed embodiments, such as those described briefly above, enable the alleviation of back pain and/or the restoration and/or treatment of adverse spinal conditions.

BRIEF DESCRIPTION OF THE DRAWINGS

According to common practice, the various features of the drawings may not be presented to-scale. Rather, the dimensions of the various features may be arbitrarily expanded or reduced for clarity. The drawings illustrate various features of at least some of the disclosed embodiments. Included in the drawings are the following figures:

FIG. 10 illustrates a front view of a vertebra with an access and a trocar inserted there through.

FIG. 11 illustrates a side view of a vertebra with a trocar inserted there through.

FIG. 12 illustrates a side view of a vertebra with a Pin inserted there through.

FIG. 13 illustrates a side view of a vertebra with an awl inserted there through.

FIG. 14 illustrates a side view of a vertebra with a drill and tube guide inserted there through.

FIG. 15 illustrates a side view of a vertebra with a tube guide inserted there through.

FIG. 17 illustrates a side view of a vertebra with a drill inserted there through.

FIG. 19 illustrates a side view of a vertebra with an implant gauge inserted there through.

FIG. 21 illustrates a side view of a vertebra with an implant and implant holder inserted there through.

DEFINITIONS

Figure 1A:
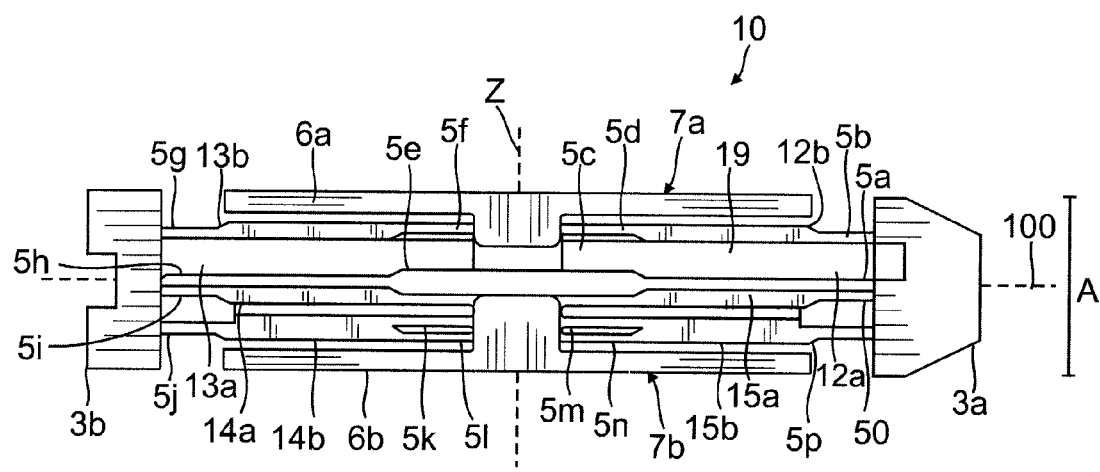
FIG. 1A illustrates a perspective view of an embodiment of an expansible implant according to the disclosure, in a resting, non-expanded position.

Before embodiments of the subject disclosure are further described, it is to be understood that the disclosure is not limited to particular embodiments described, as such may of course vary. It is also to be understood that the terminology used here in is for the purpose of describing particular exemplary embodiments only, and is not intended to be limiting. Unless defined otherwise, all technical terms used herein have the same meaning as commonly understood by one skilled in the art to which this disclosure belongs.

Where a range of values is provided, it is understood that each intervening value, between the upper and lower limit of that range, and any other stated or intervening value in that stated range, is encompassed within at least some of the embodiments of the subject disclosure. The upper and lower limits of these smaller ranges may independently be included in the smaller ranges, and are also encompassed within at least some of the embodiments of the subject disclosure, subject to any specifically excluded limit in the stated range. Where the stated range includes one or both of the limits, ranges excluding either or both of those included limits are also included in at least some of the embodiments of the subject disclosure.

Throughout this application, various publications, patents and published patent applications may be cited. The disclosures of these publications, patents and published patent applications referenced in this application are hereby incorporated by reference in their entirety into the present disclosure. Citation herein by the Applicant of a publication, published patent application, or patent is not an admission by the Applicant of the publication, published patent application, or patent as prior art.

It must be noted that as used herein and in the appended claims, the singular forms "a", "and", and "the" include plural referents unless the context clearly dictates otherwise. Thus, for example, reference to a "bearing surface" includes a plurality of such bearing surfaces, and reference to "the retaining element" includes reference to one or more retaining elements and equivalents thereof known to those skilled in the art, and so forth.

It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation. Accordingly, the term "optional" or "optionally present"—as in an "optional element" or an "optionally present element" means that the subsequently described element may or may not be present, so that the description includes instances where the element is present and instances where it is not.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

DETAILED DESCRIPTION

At least some of the embodiments of the subject disclosure include an expansible/expandable implant which may be used, according to some embodiments, to restore and/or expand the distance between two vertebrae (e.g., between two adjacent vertebrae) or to restore and/or expand the space within a vertebra (e.g., within a single vertebral body). Accordingly, embodiments of the present invention may also be used as a vertebroplasty device to treat a compression fracture(s) of a vertebral body.

The implant may include at least first and second opposed plates or other bearing members/elements (which preferably include a bearing surface) that are intended to move away from one another according to the plane of expansion as the implant is expanded. The at least first and second opposed plates may include first and second bearing surfaces, respectively. The first and second bearing surfaces may each include a recess configured for engaging a portion of at least one vertebrae (or at least one of the plates/bearing surfaces may include a recess), or the first and second bearing surfaces may not include a recess, but rather may be configured for engaging a portion of at least one vertebrae directly on the surface thereof.

The implant may additionally include at least first and second opposed end members (e.g., a distal and a proximal end member), that are associated with each of the opposed plates, and an elongated retaining element that is associated with each of the first and second opposed end members. Specifically, the opposed end members may be separated one from the other by a distance d, wherein the distance d corresponds to a length of a portion of the retaining element.

One or more of the first and second opposed end members may include an aperture, such as an aperture that extends either partially or fully through the end member. For instance, one or more of the end members may include an aperture configured for receiving a retaining element. The retaining element may, therefore, be moveably and/or removably associated with one or more of the end members.

For example, a first, e.g., distal, end member may include an aperture that extends entirely from a front surface to a back surface of the end member through which a portion of the extended retaining element may entirely pass. A second, e.g., proximal, end member may include an aperture that does not entirely pass through the length of the end member. The aperture may be such that it is configured for receiving a portion, e.g., and end portion, of the extended retaining member, but not for allowing the passage of the end member entirely through the end member. Accordingly, the second, e.g., proximal, end member may form an abutment such that the extended retaining element may be passed entirely through the first, e.g., distal end member, and extend toward and into the second, e.g., proximal, end member but not extend entirely there through. In this manner, as the distal end member is moved horizontally, e.g., in the x direction, toward the proximal the implant itself transitions from a collapsed or contracted configuration to an expanded configuration.

The implant may further include at least a pair of first and second supports. In some embodiments, the first and second supports may be associated with at least one of the first and second end members and at least one of the first and second opposed plates. In this manner, as the distance d separating the first end member from the second end member decreases, e.g., as the distal end member is translated horizontally along a length of the extended retaining element toward the proximal end member, the pair of first and second supports move axially away from a central horizontal axis corresponding to the length of the extended retaining element, thereby pushing the first and/or second opposed plates away from one another, according to the plane of expansion, resulting in the implant being expanded.

In some embodiments, the implant may include a mechanical resistance element that is configured for preventing the expansible implant from contracting once it has been expanded. For instance, in certain embodiments, the retaining element may include a mechanical resistance adapted for locking and thereby retaining the implant, once expanded, in the expanded configuration. For example, in certain embodiments, the mechanical resistance may include a retaining element, which may include a raised ridge or a notch portion (or a plurality thereof).

Specifically, in certain instances, the retaining element may be configured for interacting with at least one of the end members in such a manner that as the implant is expanded, at least a portion of the end member becomes associated with at least a portion of the retaining element, which association prevents the implant from contracting once expanded. For instance, in one exemplary embodiment, as a first, e.g., distal, end member moves forwards along the extended retaining element toward the second, e.g., proximal, end member, and the implant is expanded, the end member, contacts the noted portion of the retaining element and is thereby prevented from moving horizontally backwards away from the opposed, e.g., proximal end member. In this manner, the retaining element is adapted for retaining the implant, once expanded, in the expanded configuration, and thus the retaining element prevents the implant from contracting once expanded. Such "retaining," therefore may also be locking, that is, locking the implant in an expanded configuration.

In some embodiments, the retaining member may be configured with one or more ridges that extend outwards away from the outer surface of the retaining member. In some embodiments, the retaining member may be configured with one or more notches that extend inwards away from the outer surface of the retaining member.

In certain embodiments, the mechanical resistance may include an engagement element and an engagement element receiving member. For instance, in some embodiments, the expansible implant may include at least a pair of first and second supports that are associated with at least one of the first and second plates and additionally associated with at least one of the first and second end members, as described above, wherein at least one of the pair of the first and second supports includes an engagement element and an engagement element receiving member. For example, at least one of the first and second supports may include the engagement element, and another of the first and second supports may include the engagement element receiving member. In certain instances, the engagement element and the receiving member may be configured for associating with one another in such a manner so as to restrain the implant from contracting once expanded. In one exemplary embodiment, the engagement element may configured as a tooth element and the receiving member may be configured as a notch element.

Methods of using such expansible implants for the alleviation of back pain and the restoration and/or treatment of adverse spinal conditions are also provided herein.

As summarized above, some of the embodiments of the subject disclosure provide for an expansible implant. In some embodiments, the implants may be employed to either retain or expand the distance between two vertebrae or may be employed to either retain or expand the space within a vertebral body. Such implant embodiments include a collapsed configuration, suitable for implantation at the spine or within an intravertebral space, and an expanded configuration, for instance, where the implant retains or expands the distance between vertebrae or retains or expands the space within a vertebral body.

In some embodiments, the diameter (or minimal height) of the expansible implant in a collapsed configuration may be between about 3 mm and about 20 mm, for instance, between about 5 mm to about 15 mm, such as between about 7 mm and about 12 mm, including between about 8 mm and about 10 mm. Likewise, in some embodiments, the expansible implant may have a maximally expanded height that ranges from between about 10 mm and about 40 mm, for instance, between about 12 mm and about 20 or about 25 mm, such as between about 15 mm and about 18 mm. For instance, the height of the implant may be sized to be substantially equal to the vertebral height.

Further, due in part to the mechanical resistance of the subject implant, the implant may have a variety of configurations that range between a minimally collapsed configuration to a maximally expanded configuration. For instance, the mechanical resistance may be such that it includes a plurality of resistance elements configured for allowing the expansible implant to expand to one or more designated heights. For example, the mechanical resistance may include a plurality of ridges, notches, and engagement elements as well as engagement element receiving members. In this manner, the degree and rate of expansion of the implant may be precisely controlled by the configuration and placement of the mechanical resistance elements so as to allow the implant to be expanded in such a way as to specifically conform to an inter-vertebral space in need of correction. For instance, a suitable height of expansion may range from between about 0 mm to about 40 mm, for instance, about 5 mm and about 25 mm, such as about 6 mm and about 20 mm, including about 7 mm and about 15 mm, such as about 8 mm and about 10 mm.

According to some embodiments, the implant is used in an intervertebral application, where the implant may be configured so as to be inserted into an intervertebral space between two vertebrae (for example), or inserted between two bone segments of vertebrae (e.g., two adjacent vertebrae). For instance, in some embodiments, such as where there has been a deterioration of the intervertebral disc, an intervertebral implant according to some embodiments may be inserted, in a collapsed configuration into the deteriorated region between two vertebrae and, once appropriately positioned, may be expanded so as to restore or retain the space between the two vertebrae. In some embodiments, the implant is inserted between two spinous processes of adjacent (for example) vertebrae.

According to some embodiments, the implant is used in an intravertebral application, such as a vertebroplasty procedure, where the implant may be configured so as to be inserted into an intravertebral space within a vertebral body (for example). For instance, in some embodiments, such as where there has been a spinal fracture, such as that caused by osteoporosis, an intravertebral implant according to some embodiments may be inserted, in a collapsed configuration into the deteriorated region within a vertebral body and, once appropriately positioned, may be expanded so as to restore or retain the space within the vertebral body.

As described above, the implant according to some embodiments may have a collapsed configuration and an expanded configuration and may be moveable from the collapsed to the expanded configuration. In some embodiments, the implant in the collapsed configuration includes a tubular body, which tubular body may be manufactured of any suitable material by methods well known in the art. For instance, the body may be fabricated from biocompatible material, for example titanium, into a tubular body using lathe, laser, and/or electro-erosion manufacturing techniques (cast manufacturing may also be used).

Accordingly, in some embodiments, the implant of the subject disclosure may include one or more plates. For instance, in some embodiments, the implant includes a plurality of plates, including at least a first and a second plate in an opposed configuration to one another. A plate of the subject disclosure may have any suitable shape and have any suitable size so long as it is capable of assisting in the engagement and/or support of a body element, such as a bone or tissue. For example, in some embodiments, a suitable plate of the subject disclosure may have a width that ranges from about 2 mm to about 18 mm, such as from about 5 mm to about 12 mm, for instance, between about 7 mm and about 10 mm, such as between about 8 mm and about 9 mm. In some embodiments, the plate may have a length that ranges from about 5 mm to about 40 mm, such as from about 10 mm and about 30 mm, for instance, between about 15 mm and about 25 mm, such as between about 18 mm and about 20 mm. In some embodiments, the plate may have a thickness that may range from about 0.2 mm and about 10 mm, for instance, between about 1 mm and about 7 mm, such as between about 2 mm and about 5 mm. In one embodiment, each of a plurality of plates may form partially cylindrical support surfaces, one portion of which may be parallel to a longitudinal axis of the expansible implant. As indicated previously, some embodiments of the present disclosure, the plates may comprise any implant element that support and/or bears against the bone or other issue. Such elements need not be linear or flat in configuration, and need not be parallel to one another.

In some embodiments, the length of the implant may be sized to be substantially equal to the plate(s) and/or a support surface thereof. Such a feature allows optimization of a ratio of the support length on the bone, tissue, or other body element to the length of the implant.

In some embodiments, the plates of the implant include or act as a bearing surface (e.g., external, bone or tissue-engaging surface of a plate) configured for engaging a bone, tissue, or other body element of a subject (i.e., patient), such as a vertebral bone or vertebral or intervertebral tissue. In some embodiments, the plate/bearing-surface includes a recess, notch, and/or opening ("engaging member") which receives a portion of the bone or tissue of the cavity into which the implant is placed. Accordingly, in some embodiments, the engaging member (e.g., recess, etc.) has a morphology that is complimentary to a bone, tissue, or other body element so as to receive and/or engage the bone, etc. in a snug and/or predetermined manner.

For example, in some embodiments, the bearing surfaces each include an engaging member that is configured for engaging a portion of a respective vertebra of two vertebrae adjacent each respective plate. In some embodiments, the bearing surfaces each include an engaging member that is configured for engaging a portion of two opposing surfaces within a vertebral body. In some embodiments, the bearing surface of the plates include an extended, elongate or winged portion.

The engaging member may have any suitable shape and/or dimension so as to receive or otherwise engage a bone, tissue, or other body element. For instance, the engaging member may be round, spherical, square-like, V-shaped, parabolic, concave, convex and/or the like. Specifically, in some embodiments, the engaging member is configured as a recess, which may have a width that ranges from about 2 mm and about 12 mm, for instance, between about 4 mm and about 10 mm, such as between about 5 mm and about 6 mm. In some embodiments, the engaging member may have a length that ranges from about 5 mm and about 12 mm, for instance, between about 7 mm and about 10 mm, such as between about 8 mm and about 9 mm. In some embodiments, the engaging member may have a depth that ranges from about 2 mm and about 10 mm, for instance, between about 4 mm and about 8 mm, such as between about 5 mm and about 6 mm.

In some embodiments, the plate/bearing-surface does not include a recess, notch, or opening (e.g., an engaging element), but rather includes a substantially planar surface that contacts a portion of the bone or tissue of the cavity into which the implant is placed. Accordingly, in some embodiments, the planar bearing surface of the plate has a morphology that is capable of contacting a bone, tissue, or other body element, for instance, along a greater length of the bearing surface than would otherwise be possible if the bearing surface were to include an engaging element, such as those described above.

In some embodiments, the implant may include two opposed plates with first and second bearing surfaces, which may or may not include a recess, wherein the bearing surfaces are configured for engaging at least a portion of a restoration surface, such as a bone, tissue, or other body element surface of a subject. Accordingly, the implant may be expanded by the movement of a first and second opposing plate away from one another, when the implant is opened out, e.g., expanded. Such a feature allows the pressure which is exerted by the bearing surface of the plates of the implant on the bone, tissues, etc. to be reduced, for instance, by increasing the contact or support surface.

In some embodiments, the implant may include one or more end members, which may be integral with the implant. For instance, in some embodiments, the implant includes a plurality of end members, such as at least a first and a second end member in an opposed relationship and spaced apart from one another.

An end member, in some embodiments, may have any suitable shape and any suitable size so long as the end member is capable of associating with one or more of a plate and/or other end member so as to facilitate the expanding and/or retaining of the expansible implant into a desired configuration. For example, an end member may be round, circular, triangular, pyramidal, square, etc. In some embodiments, a suitable end member of the subject disclosure may have a width or diameter that corresponds to the width or diameter of the implant, and such width/diameter may be within a range of about 5 mm and about 15 mm, for instance, between about 6 mm and about 12 mm, such as between about 8 mm and about 10 mm. In some embodiments, each end member may have a length that ranges about 1 mm and about 5 mm, for instance, between about 2 mm and about 4 mm, such as about 3 mm. In some embodiments, the end member may have a thickness that may range from about 0.5 mm and about 5 mm, for instance, between about 1 mm and about 4 mm, such as between about 2 mm and about 3 mm.

In some embodiments, the implant may include a retaining element. The retaining element according to some embodiments, may have any suitable shape and any suitable size so long as the retaining element is capable of interacting with one or more of the end member(s) and/or plate(s) of the implant, described above, so as to facilitate the expanding, contracting, and/or retaining (and may include locking of the implant) of the implant into a desired configuration. For example, a retaining element may be an elongate member that may be round, circular, triangular, pyramidal, square, rectangular, etc. It may be tubular and solid, tubular and hollow, or a combination thereof. In some embodiments, a suitable retaining element may have a body with a proximal portion, a distal portion and an extended body there between.

In certain embodiments, the retaining member may be elongated, tubular, and may include a lumen therein. For instance, the retaining member may include a tubular body with an outer surface and an inner surface, wherein the inner surface bounds a lumen or passage way. Accordingly, in some embodiments, the tubular body is configured for receiving and/or passing a fluid through the body of the retaining member. The retaining member may additionally include one or more apertures configured for allowing the egress of a fluid there through.

Hence, in certain instances, the retaining element is configured for delivering a fluid, such as a bone cement, through the expansible implant to a site of delivery. For example, in some embodiments, the distal portion of the extended body is configured for associating with an expander and/or fluid delivery device, wherein the expander is capable of both facilitating the expansion of the expansible implant and/or may further be capable of transmitting a fluid from a fluid reservoir to the interior of the retaining member and subsequently out through a delivery aperture, such as an aperture positioned at a proximal portion of the retaining member. One or more apertures may be included, wherein the apertures may be any suitable size, shape, and/or configuration as desired. They may be spaced regularly or randomly around the circumference of the tubular body of the retaining member.

The proximal and/or distal portions of the retaining element may be configured for engaging and/or moveably associating with one or more end members. For instance, the extended body may be configured for passing through an aperture(s) in one of the opposed end members and may further be configured for contacting and associating with the other opposed member. For example, a proximal portion of the extended end member may pass through an aperture in a first end member and may further be configured for passing through an aperture in the second opposed member. In certain instances, the proximal portion of the retaining member passes entirely through an aperture in the first opposed end member and extends toward and contacts the second opposed end member, but does not pass entirely there through.

Accordingly, in some embodiments, the end member includes an aperture, such as an aperture configured for receiving a portion of a retaining element. For instance, in some embodiments, the end member(s) includes an aperture configured for receiving one end of a retaining element. Specifically, in some embodiments, the end member includes a proximal surface and a distal surface and includes at least a first aperture provided therein, wherein the aperture extends there through from the proximal surface to the distal surface. In some embodiments, the aperture includes a mating area, which may include a mating surface, where the mating area is configured for mating with a respective mating portion of a retaining element.

Further, in some embodiments, the end member includes a proximal and/or distal surface, which may further include a recess, such as a recess configured for receiving a portion of a retaining element. Specifically, in some embodiments, the proximal surface of an end member includes a recess, wherein the recess surrounds an aperture and is configured for receiving the proximal portion of a retaining element such that when a distal portion of the retaining element is fully received within the aperture, the proximal portion of the retaining element (e.g., the head portion) does not extend beyond the bounds or plane of the proximal surface of the end member. Rather, the head portion of the retaining element aligns within the recess so as to be flush with the proximal surface of the end member. In some embodiments, the one or more surfaces of the end member may include a recess, notch, or over-hang region, such as a notch and/or over-hang that is adapted to engage and/or otherwise receive a portion of an implantation installation device, such as an implant expander.

An aperture of an end member may be of any suitable shape and of any suitable size, so long as it is configured so as to receive a retaining element and/or snugly fit a retaining element there through. Such apertures may include a mating surface that includes screw threads which correspond to screw threads of a retaining member. For instance, in some embodiments, the aperture is circular or round and includes a diameter that ranges from about 1 mm and about 6 mm, for instance, between about 2 mm and about 5 mm, such as between about 3 mm and about 4 mm. It is worth noting that one or both end members may include apertures with mating areas, e.g., threading, therein. For example, where the retaining element may be an elongated, shaft member that includes a mating surface that includes threading, the apertures of both end members may include threading, or the aperture of only one end member (e.g., distal end member) may include threading.

In some embodiments, the proximal and/or distal portions of the retaining element may include an abutment and/or a mating area with a mating surface, wherein the abutment and mating areas of the retaining element are configured for being associated with corresponding mating areas of end members and/or the apertures thereof. For instance, in some embodiments, a proximal or distal portion of a retaining element may include an abutment, wherein the abutment is configured for associating with an end member, for example, an exterior side of a proximal end member. In some embodiments, a proximal or distal portion of a retaining element may include a mating area, wherein the mating area is configured for associating with a corresponding mating surface of an end member, for example, a corresponding mating area of an aperture positioned within the end member. Such mating areas may be corresponding screw threads, and may also be a rivet-like configuration. In certain embodiments, neither the retaining element nor the end member(s) include corresponding mating surfaces that include screw-threads and/or rivet configurations, or the like.

In some embodiments, the retaining element has an elongate body that has a diameter that ranges from about 1 mm and about 6 mm for instance, between about 2 mm and about 5 mm, such as between about 3 mm and about 4 mm. In some embodiments, the elongate body of the retaining element may have a length that ranges from about 10 mm and about 45 mm, for instance, about 15 mm and about 30 mm or about 25 mm, such as about 18 mm and about 20 mm.

In some embodiments, the retaining element has an extended tubular body that is configured for moveably or non-moveably associating with one or more of the opposed end members. For instance, in one embodiment, the extended body of the retaining member may have a portion, such as a proximal portion, that includes an abutment portion, which abutment portion may be configured for preventing the substantial horizontal movement of the retaining member relative to the end member. Accordingly, in some instances, the abutment portion may be in any form so long as it is configured for contacting a proximal end member and adapted for preventing the passage of the retaining element through the end member. In such an embodiment, the abutment is configured for facilitating the association of the proximal portion of the retaining element with the end member. In some embodiments, the abutment portion may include a raised mating surface.

Further, in one embodiment, the extended body of the retaining member may have a portion, such as a distal portion, that is configured for moveably associating with a distal end member. For instance, in certain embodiments, an end member, such as a distal end member, may be adapted for being fitted over the retaining element and configured for moving, e.g., sliding, in the horizontal direction (defined by an axis corresponding to the length of the extended body of the retaining member) toward the opposing end member, e.g., the proximal end member. In this manner, the distance d between the proximal and distal opposed end members may be modulated by the movement of one end member, e.g., a distal end member, horizontally along the length of the retaining element toward a second, opposed end member, e.g., a proximal end member.

In certain embodiments, the retaining element includes engagement elements such as a raised ridge or a notch portion. In certain instances, the retaining element and at least one of the end members may be configured for interacting in such a manner that as the implant is expanded, at least a portion of the end member becomes associated with at least one portion of the retaining element, which association prevents the implant from contracting once expanded. Accordingly, in certain embodiments, as a first, e.g., distal, end member moves along the extended retaining element, and the implant is expanded, the end member, or a portion thereof, contacts an engagement element, or a portion thereof, and is thus prevented from moving horizontally away from the opposed, e.g., proximal, end member. In this manner, the retaining element retains the implant, once expanded, in the expanded configuration, and thus the retaining element prevents the implant from contracting once expanded. Such "retaining," therefore may also be locking, that is, locking the implant in an expanded configuration.

In some embodiments, the retaining element is elongated and includes a shaft (for example, a solid or hollow tube-like shaft) having threading on its proximal and/or distal portion(s). This threading may correspond to threading positioned internally on an aperture of an end member, such as a corresponding proximal and/or distal end member. To that end, for example, where a proximal end of a retaining element containing threading is inserted through an aperture in the distal end member (the aperture of the distal end member may or may not include screw threads) and into the aperture of a proximal end member, where the proximal end member includes threading that corresponds to the threading on the proximal portion of the retaining element. In such a configuration, the retaining element is enabled to retain the implant in an expanded configuration with the proximal end portion of the retaining element being screwed into the proximal end member, and the underneath side of the screw head located on the distal portion of the retaining element abutting the outer distal surface of the proximal end member.

In some embodiments, the retaining element has an extended wire-like configuration, where the wire may include a proximal portion with a proximal end, a distal portion with a distal end, and an elongate body portion extending between the proximal and distal portions. A distal portion, e.g., a distal end, of the wire may include a retention member, such as a hook like configuration or screw, where the hook is adapted for engaging at least a first portion of a first aperture (located on the distal end member of the implant) such that upon the implant being expanded to a desired expanded state an abutment may be formed on a proximal end of the wire.

Hence, in some embodiments, the expansion of the implant may be effectuated, in part, by the movement of the first end plate, along the retaining element, toward the second end member such that the distance d between the two opposed end members decreases. Accordingly, in some embodiments, the implant includes a plurality of opposed end members that are associated with both a plurality of opposed plates and a retaining element, which together are configured such that as the end members are drawn together (e.g., the distance between the end members decreases longitudinally), the implant expands in a direction perpendicular to a longitudinal axis of the implant. In some embodiments, such expansion may be radial e.g., within a single plane of expansion.

In some embodiments, an expansible implant includes one or more supports for one or more of the opposed plates, and/or may include one or more material webs or plastically deformable zones/areas, which may be associated with one or more of the supports and/or the opposed plate(s) and/or one or more opposed end members. In certain instances, one or more such webs/zones may be associated with one or more supports. For instance, in some embodiments, the implant includes a plurality of supports, such as at least a first and a second support, which support may be directly or indirectly associated with a plate, and/or bearing surface thereof, and/or an end member(s). For example, in some embodiments, an expansible implant includes first and second plates that include first and second bearing surfaces, where the implant additionally includes first and second supports that are associated with each of the first and second plates and/or bearing surfaces thereof. In some embodiments, the first and second supports are further associated with first and second end members. In some embodiments, the first and second supports comprise a plurality of first and second supports.

Some embodiments of the disclosure may also be used with spinal implant devices which do not utilize plastic deformation in expansion of the implant. To that end, any expansion of such implants which do not include such plastic deformation, rely on the retaining element (according to some embodiments of the disclosure) for retaining the implant in an expanded configuration.

In some embodiments, the implant includes first and second supports for each of the first and second bearing surfaces of the plates, wherein the supports are positioned under each plate, respectively. In some embodiments, the opening out of the first and second plates includes the raising of the plates via the use of the one or more supports positioned under the plates. Such a feature may allow thrust forces to be distributed under the plate in order to reduce the cantilever.

A support of the implant may be of any suitable dimension so long as it is capable of being associated with one or more of a plate and an end member, and in some embodiments, either directly or indirectly associating the support with the end member, and thereby serving the purpose of supporting a plate of the implant. Specifically, in some embodiments, a suitable support of the subject disclosure may have a width that ranges from about 5 mm and about 12 mm, for instance, between about 6 mm and about 10 mm, such as between about 8 mm and about 9 mm. In some embodiments, the support may have a length that ranges about 5 mm and about 12 mm, for instance, between about 6 mm and about 10 mm, such as between about 8 mm and about 9 mm. In some embodiments, the support may have a thickness that may range from about 0.2 mm and about 2 mm, for instance, between about 0.5 mm and about 1.5 mm, such as between about 1 mm and about 1.25 mm.

In some embodiments, where a plurality of supports are associated with a plurality of plates, the supports may all have the same length or be of one or more different lengths. For instance, the plurality of supports may have substantially equal lengths, or alternatively, at least one of a first and second support is shorter in length to a corresponding support, such that upon expansion of the implant, the first and second supports move at an angle toward one another.

The material web(s) (also may be referred to as zone(s), area, and the like) as briefly described above, may be used to control expansion of the implant. The material web/zone may have any suitable configuration so long as it is capable of facilitating the association of a support with a plate and/or end member and is adapted for being deformed, for instance, plastically, so as to control the expansion of the implant. Accordingly, in some embodiments, the material web controls the expansion of the implant by deforming in a predetermined manner to a predetermined extent.

In some embodiments, the material web/zone is an articulation area formed by the thinning of a wall that is interposed between a support portion and a plate and/or end member. Accordingly, the material web may be formed by the production of a weakened zone at a region of connection between a support and a plate and/or end member, for instance, by fabricating a groove in the support material the thickness of which is determined by the depth of the groove, whereby the weakened zone allows the articulation and/or support to be plastically deformed without breaking.

In some embodiments, the material web is positioned between each support and a corresponding plate and/or end member, where the material web includes a predetermined thickness which controls the expansion of the implant. As stated earlier, in some embodiments, the web/zone corresponds to an expansion controlling element(s) for controlling a determined expansion value of the implant, between a minimum height/diameter of the implant before any expansion and a maximum height/diameter of the implant after its maximum expansion.

In certain instances, the expansible implant may include a retaining element/member. The retaining member may be any member configured for retaining the expansible implant from contracting, or otherwise collapsing, once the implant has been expanded. For instance, in certain embodiments, the retaining member may include one or more ridges, such as a ridge that spans at least a portion of the circumference of the retaining member. For example, the ridge may be a portion of the retaining member that extends outwardly away from the outer surface of the retaining member. The ridge may span, e.g., circumscribe, the entire circumference of a portion of the outer surface of the retaining element or may span one or more portions of the retaining member.

In some embodiments, the retaining member may include one or more notches, such as a notch that spans at least a portion of the circumference of the retaining member. For example, the notch may be a portion of the retaining member that extends inwardly away from the inner surface of the retaining member. The notch may span, e.g., circumscribe, the entire circumference of a portion of the inner surface of the retaining element or may span one or more portions of the retaining member.

In certain embodiments, the retaining member includes a proximal portion with a proximal end, and a distal portion with a distal end. In certain instances, the retaining member is positioned at one or more of the proximal and/or distal portions. In certain embodiments, the retaining element may further include a configuration adapted for allowing a proximal and/or distal portion of the retaining member to deform, such as in response to a force. For instance, in certain instances, the retaining element includes one or more engagement elements positioned at a distal portion of the retaining member, which distal portion is configured for deforming.

A deformation configuration may be any configuration so as to allow at least a portion of the retaining member to deform, such as in response to a force or pressure applied to the retaining member. In certain instances, the deformation configuration is such that it allows a portion of the retaining element to deform in response to the expansion of the implant. In some embodiments, the deformation configuration may be an opening, such as a window. The opening or window may have any suitable shape, such as a circle, triangle, square, rectangle, oval, u-shape, or the like.

In some embodiments, one or more of an end member(s), retaining element, engagement elements, and deformation configuration are configured for acting with one another in such a manner so as to restrain the expansible implant from contracting or otherwise collapsing once the implant has been expanded. For instance, in certain embodiments, the expansible implant includes a system that includes an extended retaining element, the extension of which includes a horizontal axis defined as x, an engagement element, and one or more end members, wherein at least one of the end members is capable of moving relative to the retaining element and/or opposing end member (if included)). In certain instances, the end member of the system is configured for moving horizontally along the x axis, e.g., from a point a to a point b (defined herein as the "forward" direction) of the retaining element, and interacting with the retaining member, such that as the end member contacts, or otherwise engages the retaining member, the retaining member is engaged and prevents movement of the end member in the "backwards" direction, for instance, from point b to point a. In this manner, the expansible implant may be expanded, for instance, by movement of the moveable end member in the forward direction, e.g., toward an opposing end member; and the expansible implant may be prevented from contracting by the interaction of the moveable end member with the retaining member, which interaction causes the engagement of the retaining member, which engagement, in turn, prevents the movement of the moveable end member in the backwards direction, e.g., away from the opposing end member.

In certain instances, an end member may include a configuration adapted to allow the end member to interact with the retaining member so as to facilitate the ability of the retaining member to prevent the expansible implant from contracting once it has been expanded. For instance, the end member may include a ridge, such as a portion of the end member that extends outwards or inwards (e.g., tapers) away from a plane defined by an outer surface of the end member, wherein the ridge is configured for associating with a corresponding engagement element of the retaining member in such a manner as to keep the implant from contracting once expanded. Accordingly, in certain embodiments, expansion of the implant may be coincident with the movement of an end member over one or more engagement elements of the retaining element, which function to prevent the implant from collapsing once expanded. Where one or a plurality of engagement elements are included, the degree of expansion can be modulated by the movement of an end member over one of the one or more of the engagement elements (i.e., movement over and relative to the retaining element).

In some embodiments, the disclosed implant includes an extended retaining element, however, the retaining element does not include a retaining element/member. Rather, as set forth above, the expandable implant may include at least a pair of first and second supports. For instance, the expansible implant may include a pair of first and second supports that are associated with at least one of the first and second plates and may additionally be associated with at least one of the first and second opposed end members.

In some embodiments, one or more of the first and/or second supports may include one or more engagement elements. For instance, in certain instances, at least one of the pair of the first and second supports includes a first engagement element and a second engagement element, where the two engagement elements interact to retain the implant in an expanded configuration. An engagement element may be any suitable element that is capable of being associated with at least one member of a pair of supports and configured for interacting with a second member of a pair of supports in such a manner as to prevent the further movement of the one support relative to the other in at least one direction. For instance, in some embodiments, the engagement element may be configured as one or more protrusions or teeth, that are capable of associating with a corresponding support member, or portion thereof, so as to engage the support member and prevent relative movement between the two support members in at least one direction. An engagement element receiving member may be any suitable member that is capable of being associated with at least one support member of a pair of support members, e.g., a support member that does not include an engagement element, and configured for interacting with an engagement element, e.g., positioned on the second member of the pair of supports, so as to facilitate the ability of the engagement element for preventing the movement of one support relative to the other support in at least one direction. For instance, in some embodiments, the engagement element receiving member may be configured as one or more notches defining a cavity, such as a notch that is adapted to receive a tooth within a cavity thereof, which notch is positioned on one of a pair of supports and is adapted for receiving at least a portion of an engagement element positioned on a corresponding support. For example, at least one of the first and second supports may include the engagement element and another of the first and second supports may include the engagement element receiving member. In certain instances, the engagement element and the receiving member may be configured for associating with one another in such a manner so as to prevent the movement of one of the pair of first and second supports from moving with respect to the other member of the pair, and thereby keeping the implant from contracting once expanded.

For instance, in certain embodiments, the expansible implant includes a pair of opposed plates with bearing surfaces, a pair of opposed end members, a retaining element, and a pair of first and a second supports, wherein one of the pair of first and second supports connect one of the opposed plates with one of the opposed end members (e.g., a distal end member), and the other of the pair of first and second supports connect another of the opposed plates with another of the opposed end members (e.g., a proximal end member). In such an instance, the end members, supports, opposed plates, and retaining element, may be configured such that as one of the end members, e.g., the distal end member, moves along the retaining element toward the proximal end member, the supports move axially away from the outer surface of the retaining element thereby pushing the opposed plates outwards and away from one another. Where at least one of the first and second supports include an engagement element and the other of the first and second supports includes an engagement element receiving member, as the implant is expanded, the engagement element on a first support becomes associated with an engagement element receiving member on a corresponding second support, which association functions to restrain the implant from contracting once expanded.

As will be described in more detail below, in some embodiments, a filling material may be injected in and/or around the implant during its expansion or after it has been expanded. For instance, in certain embodiments, the expansible implant may include a retaining element wherein the retaining element includes an extended body that is tubular and includes a lumen or passage extending at least a portion of the length of the extended body of the retaining element. The extended body may additionally include a proximal and distal portions, wherein one or more of the proximal and distal portions include an opening. In certain instances, the lumen is of a dimension such that a fluid may flow through into an opening at one end of the retaining element, e.g., a distal portion, through a length of the retaining member, and out of another opening, such as an opening at a proximal portion of the extended body. Accordingly, the retaining member may be tubular and may include a plurality of openings separated by a length, which length defines a lumen, wherein one of the openings is configured for receiving a fluid and the second opening forms an aperture configured for allowing the egress of a fluid that enters through the first opening, traverses the length of the lumen toward and out of the second opening. An injection pressure of such a filling material is preferably low so as to avoid having the filling material be injected into inappropriate tissues such as blood vessel walls (or out of an intravertebral body, for example).

Such a material may be a filler cement (or in some embodiments may be a silicone or any biocompatible soft or hard material) which may aid/assist in compressive load with the implant. Cements that may be used with the implants may include an ionic cement, in particular a phosphocalcic cement, an acrylic cement, a compound of the latter, and or any other suitable cement well known in the art.

In certain embodiments, one or more of the end members may be configured for being associated with one or more of an implant expander and/or a fluid delivery device, such as an injector. For instance, in certain embodiments, an implant expander and end member and/or fluid delivery system is provided. Such a system may additionally include a fluid injection assembly, such an assembly may include a fluid injection member (e.g., an injector), a fluid reservoir, and/or a pumping mechanism. The implant expander may include an extended body having a proximal and a distal portion, wherein one end portion, e.g., a distal portion, of the extended body is adapted for being associated with one or more of an end member and/or a retaining element of an expansible implant and through that association is capable of effectuating expansion of the implant.

As set forth above, in certain embodiments, the end member may include a recessed portion and/or may additionally include one or more over-hang portions. The recessed portion may be adapted for receiving a distal portion of the implant expander, and the over-hang portion may be adapted for receiving an extended edge portion of the implant expander, such that the end portion of the implant expander fits within the recessed portion of the implant, and the extended edge portion of the implant expander fits within and/or under the overhang portion of the end member. In this manner, the implant expander may be fit within the recessed portion of the end member, may engage the one or more over hang portions, and may then be employed to expand the expansible implant from a closed configuration to an expanded configuration, for instance, by transmitting a force on the engaged end member, which force causes the end member to move horizontally along a retaining member toward an opposing implant thereby resulting in the expansion of the implant.

In some embodiments, a proximal portion of the implant expander includes a configuration for allowing the implant expander to additionally be associated with a fluid injection assembly. For instance, the proximal portion may include an expanded portion and one or more wings, such that the implant expander is capable of being coupled to a fluid injection member, such as an injection member having a complementary configuration. In certain embodiments, the proximal portion may include a luer lock connection. Additionally, a distal portion of the implant expander may include a configuration for allowing the implant expander to be associated with a retaining element of an expansible implant, such that a fluid that is transmitted into the proximal portion of the implant expander, e.g., from an injection member, may be traversed through the implant expander and into a passageway in the retaining member and thereby delivered to a cavity, such as a cavity wherein the implant is positioned. In this manner, a fluid, such as a bone cement, may be passed, e.g., pumped, from a reservoir, through the lumen of an injector and into the implant expander, wherein the fluid may then be transmitted from the implant expander to a retaining member of an expansible implant, through the retaining member, and out of an aperture of the retaining member, such as an egress aperture, positioned at a proximal (or distal) portion of the retaining member.

In some embodiments, an expansible implant may include one or more envelope members. For instance, the implant may include an expandable envelope member comprising a balloon element that is adapted for at least partially or fully covering the implant (e.g., the implant is "enveloped" within the balloon).

In some embodiments, the envelope member is capable of being expanded by the expansion of the implant from a collapsed to an expanded configuration. In some embodiments, the envelope member is configured for being expanded or further expanded by the insertion of a fluid or material, e.g., a fluid of particulate matter. The envelope member may be fabricated by means known in the art and may be fabricated from any suitable material, such as, for example, silicon, polymers, and the like.

As summarized above, the expansible implants of the present disclosure are useful for restoring vertebral bone anatomy either within a deteriorated vertebral body or between vertebral bodies. Reference will now be made in detail to various embodiments of the disclosure, which are illustrated in the accompanying figures.

Referring now to FIGS. 1-7, the expansible implant 10 represented therein may include one or more of the following. The expansible implant may include an expansion plane 2, which may be intrinsic to the implant. The implant may include an end member(s) (e.g., 3a and 3b), which end member(s) may be used for positioning the expansible implant between two surfaces, such as two opposed restoration surfaces of bone, and facilitating the expansion of the implant along a plane of expansion between the two surfaces. The implant may additionally include a first and/or second opposed plate(s) (e.g., 6a and 6b), which plate(s) is configured for moving axially away from a central (e.g., longitudinal) axis defined by line 100, and may include a bearing surface, e.g., 7a or 7b. As depicted, the opposed plate(s) does not include a recess therein, however, as described above, in certain embodiments, one or more of the opposed plates may include a recess, such as a recess that is configured for engaging a portion of a restoration surface, which as indicated above may be a portion of a bone.

Additionally, the expansible implant 10 may include one or more of the following. A support(s) (e.g., pairs of first and second supports, such as 12, 13, 14, and 15), which support(s) may be associated with one or more of a plate or end member, and may be configured for assisting in the opening out (i.e., expanding) of the expansible implant in the expansion plane 2. A material web or plastically deformable zone/area (e.g., 5a-5p) may also be included, which material web may be included, for example, for at least partially controlling the expansion of the implant, e.g., controlling expansion of the opposed plates of the implant to a determined expansion value, such as between a minimum thickness/diameter A of the implant before expansion, and a maximum thickness/diameter B of the implant after its maximum expansion. It is to be noted, that although as depicted the expansible implant includes a plurality of material webs, in certain embodiments, as described above, one or more of the depicted material webs may be absent. A retaining element (e.g., 19) may be included as well, wherein the retaining element may be associated with one or more end members. In addition to a support and/or a retaining element, the expansible implant may further include a mechanical resistance, such as an engagement element(s). For instance, the retaining element and/or support may include an engagement element that is adapted for retaining the implant in an expanded configuration once expanded.

Figure 1B:
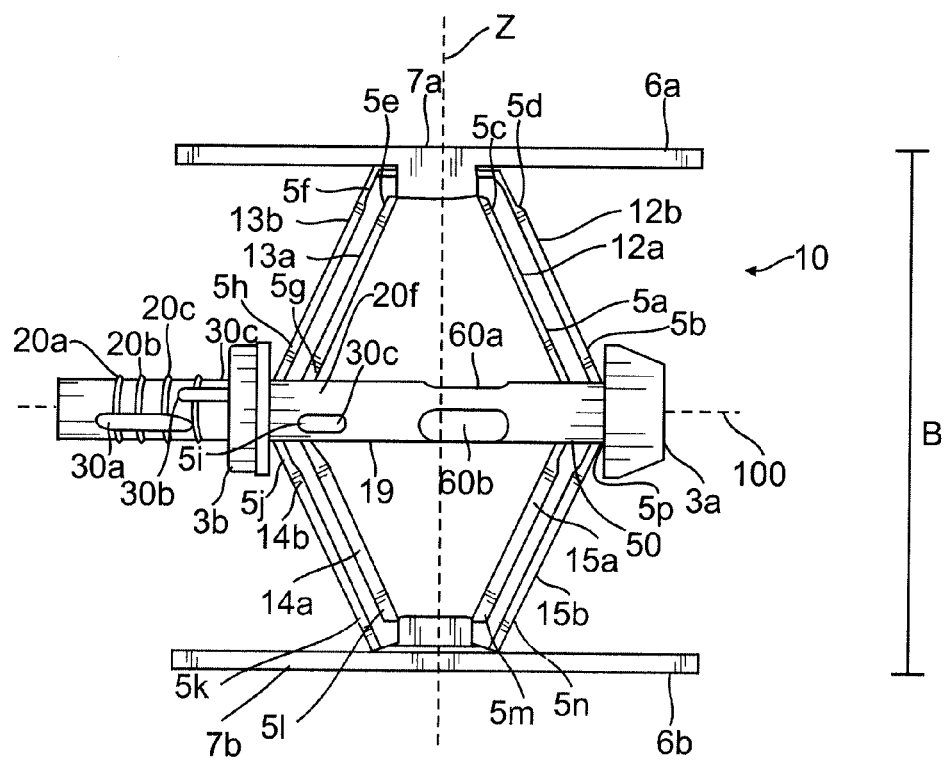
FIG. 1B illustrates the example of FIG. 1A, in opened-out, expanded position.

As shown in FIGS. 1A and 1B, implant 10 may include a cylindrical shape with a transverse circular exterior section. The implant 10 may include first 3a and second 3b end members, which adopt the shape of a transverse section of the tubular (for example) body. One or more of the end members, e.g. 3b, is moveable and may be brought towards the other end member, e.g., 3a, to allow the opening-out/expansion of the implant, as represented in FIG. 1B. The implant also includes first 6a and a second 6b opposed plates, which opposed plates include/form first 7a and second 7b bearing surfaces that are intended to be moved apart one from the other along the expansion plane 2 during expansion of the implant 10 (e.g., as end member 3b is moved toward end member 3a). Additionally, the implant includes supports 12-15, which supports include material web zones 5a to 5p. A retaining element 19 is also included.

Accordingly, the two end members 3a, 3b may be associated with each other by one or more of a material web/zone/area 5, support(s) 12-15, plate(s) 6, and/or retaining element 19. For instance, opposed end members 3a and 3b may be associated with one another either directly or indirectly via a plurality of opposed plates 6a and 6b, which plates may be parallel to central axis 100 when the implant is unexpanded and formed longitudinally in the tubular body. At least one of the two end members, e.g., 3a, may be configured for moving toward the opposed end member, e.g., 3b, horizontally, e.g., longitudinally, along the retaining element 19. Further, the plates 6a,b may be coupled with a plurality of pairs of supports 12a,b-15a,b, which supports may be interposed between the plates 6a,b and the end members 3a,b and may be configured to be folded under the plates such that as one or more of the end members (e.g., 3b) is moved toward the other opposed end member (e.g., 3a), the pairs of supports 12-15 are moved axially away from central axis 100, thereby distancing the first 6a and second 6b opposite plates from the longitudinal axis 100 of the retaining element 19 and expanding the implant 10.

As represented in FIGS. 1A and 1B, in order to allow the plates 6a and 6b to be opened out in an expansion plane 2 (passing through the longitudinal axis 100 of the tubular body), the plates 6a and 6b may be diametrically opposed. For instance, the plates 6a and 6b may be formed from a transverse recess of the tubular body 24, traversing the tubular body throughout, and extending over the length of the tubular body between the two end members 3a and 3b of the implant 10. Each plate 6a and 6b may form a system of successive rigid and deformable parts that may be articulated together in conjunction with the end members 3a and 3b, in some embodiments, as follows.

With respect to the upper plate 6a, a pair of first and second rigid supports 12a,b are connected at one end to end member 3a by means of an articulation, e.g., material web/zone 5a,b. The other end of rigid support 12a,b is connected to a first end of plate 6a by means of an articulation, e.g., material web/zone 5c,d. The second end of plate 6a may be connected at a second end to a second pair of rigid supports 13a,b by means of an articulation, e.g. material web/zone 5e,f. The other end of the second rigid support 13a,b may be connected to end member 3b by means of an articulation, e.g., material web/zone 5g,h. In some embodiments, the articulations 5a-h may include one degree of freedom in rotation, acting, respectively, about axes which are perpendicular to the expansion plane 2. Further, articulations 5a-h may be formed by a thinning of the wall forming the member in the relevant articulation zone.

With respect to the lower plate 6b, a pair of first and second rigid supports 14a,b are connected at one end to end member 3b by means of an articulation, e.g., material web/zone 5i,j. The other end of rigid support 14a,b is connected to a first end of plate 6b by means of an articulation, e.g., material web/zone 5k,l. The second end of plate 6b may be connected at a second end to a second pair of rigid supports 15a,b by means of an articulation, e.g. material web/zone 5m,n. The other end of the second rigid support 15a,b may be connected to end member 3a by means of an articulation, e.g., material web/zone 5o,p. In some embodiments, the articulations 5i-p may include one degree of freedom in rotation, acting, respectively, about axes which are perpendicular to the expansion plane 2. Further, articulations 5i-p may be formed by a thinning of the wall forming the member in the relevant articulation zone.

Additionally, a retaining element 19, spans the implant and may be moveably associated with one or more of end members 3a and 3b, such that as the retaining element 19 and/or end member 3b is engaged, end member 3b moves along retaining element 19 toward end member 3a, for instance, longitudinally along central axis 100, thereby causing supports 12a,b-15a,b and articulations 5a-5p to fold under plates 6a and 6b and thereby causing plates 6a and 6b to move axially away from central axis 100 and away from one another along an expansion plane 2, thereby causing the implant to expand, as depicted in FIG. 1B.

The displacement of the articulations may establish a rotation couple (for example) on the rigid parts of supports 12 and 13, when a force is applied to bring the end member 3a toward end member 3b along the longitudinal axis 100 of the implant. This displacement tends to make the rigid supports 12 and 13 pivot away from the longitudinal axis of the implant as a result of moving the plate 6a away from the longitudinal axis 100. The same holds for the elements of lower plate 6b, which may be constructed in a similar manner as the upper plate and may be symmetrical to the upper plate 6a with respect to a plane which is perpendicular to the expansion plane 2 passing through the longitudinal axis 100.

Thus, according to some embodiments of the present disclosure, the articulations of the upper 6a and lower 6b plates may be formed by weakened web/zones/areas produced by grooves. The grooves may define the thin material web/zone forming the tubular body of the implant, the thickness of which may be determined by the depth of the grooves in order to allow elastic deformation and/or plastic deformation of the material web/zone/area without breaking. Specifically, the rigid parts of supports 12 and 13 of the upper plate 6a, and their symmetrical zones on the lower plate 6b, e.g., 14 and 15, can adopt a position, termed extreme expansion, in which the intended rigid supports are perpendicular to the longitudinal axis 100 of the implant 10, when the end members 3a and 3b are brought one towards the other such that the implant is opened up until its maximum expansion capacity, resulting in elastic deformation and/or plastic deformation of the corresponding web material. The width of the grooves may be pre-determined to allow such a clearance of the parts of the upper and lower plates and also to impart a suitable radius of curvature to the webs in order to ensure elastic deformation and/or plastic deformation without rupture of the material.

The first 6a and second 6b plates may form first 7a and second 7b bearing surfaces, respectively, each having a length that may be substantially equal to the length of the implant and which may be displaced perpendicularly to the longitudinal axis 100 during expansion. The first 7a and second 7b bearing surfaces may each be configured so to engage and/or support a portion of a bone, tissue, or other body portion, for instance, along a plane of expansion between two surfaces, e.g., bone portions. According to some embodiments of the disclosure, since the implant 10 is formed in a tubular body, the first 6a and second 6b plates form, respectively, curved support surfaces and are parallel to the longitudinal axis 100. Each plate 6a and 6b may open out such that the bearing surfaces 7a and 7b move away from the longitudinal axis 100 of the implant pushed by the adjacent rigid supports (e.g., 12a,b, 13a,b, 14a,b, and 15a,b), when the ends 3a and 3b of the implant are brought one towards the other, and in some embodiments, by effectuation of the retaining element 19.

Figure 2A:
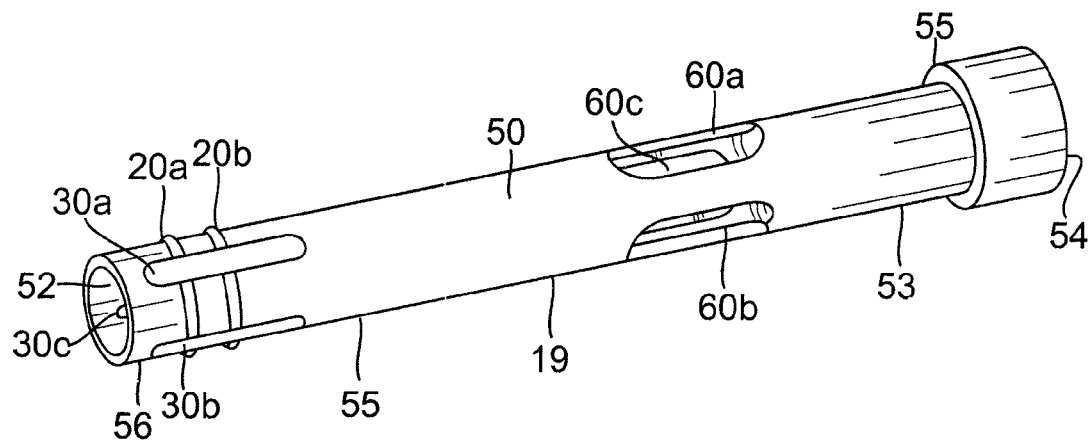
FIG. 2A illustrates a perspective view of an embodiment of a retaining element according to the disclosure.
Figure 2B:
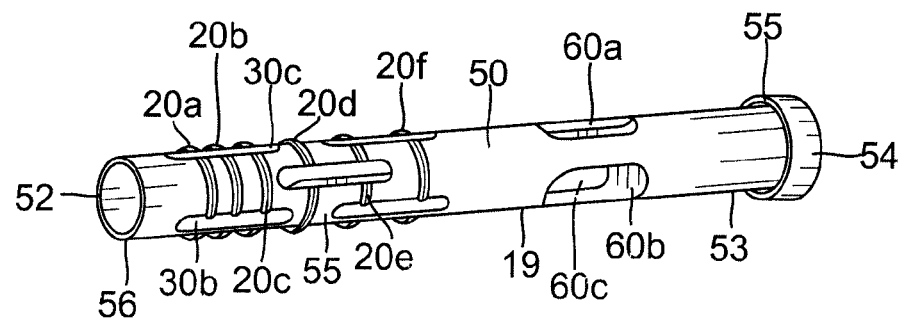
FIG. 2B illustrates a side-perspective view of the embodiment of an retaining element of FIG. 2A according to the disclosure.

As can be seen with reference to FIGS. 2A and 2B, the expansible implant 10 of the disclosure may include a retaining element 19, which retaining element includes a mechanical resistance. The retaining element 19 may include one or more of an engagement element 20, a deformation configuration 30, and/or an egress aperture 60. For instance, as depicted in FIGS. 2A-2B, the retaining element 19 may be an extended body 50 that includes a passage 52 extending therethrough, and additionally may include a proximal portion 53 with a proximal end 54, and a distal portion 55 with a distal end 56. Additionally, as can be seen with reference to FIGS. 2A and 2B, the retaining member (19) may include one or more apertures (60) configured for allowing the egress of a fluid that is passed through the passage (52) of the retaining element (19).

As can be seen with reference to FIGS. 2A and 2B, the shape and configuration of the retaining element may vary. In FIG. 2A, the retaining element 19 has a relatively smooth and planar outer surface that has a distal portion 55 that includes two engagement elements 20a,b. The distal portion 55 of the retaining element 19 additionally includes three deformation configurations 30a-c, which are shaped like three elliptical windows. The deformation windows 30a-c may be configured such that as the implant 10 expands, for instance, as one end member, e.g., 3b, moves toward the opposing end member, e.g., 3a, one or more of the deformation windows 30a-30b become disfigured, or otherwise contracted, thereby allowing the end member, e.g., 3b to pass over the engagement elements 20a,b (i.e., in the forward direction), thus allowing the implant 10 to expand. However, because of the design of the engagement elements and/or deformation windows, movement of the end member, e.g., 3b, is only permitted in the forward direction, e.g., toward the opposing end member, e.g., 3a. Hence, once the end member, e.g., 3b, has traversed over the engagement element, e.g., 20a, toward the opposing end member, e.g., 3a, movement of the end member, e.g., 3b, backwards, e.g., away from the opposing end member, e.g., 3a, is prohibited by the engagement element, e.g., 20a. A proximal portion 53 of the retaining element 19 includes three egress apertures, that are also configured as elongated windows and are adapted to allow the egress of a fluid from within the passage 52. In FIG. 2B, the retaining element 19 is similar to that of FIG. 2A, however, the retaining element includes 6 different engagement elements, 20a-f. Accordingly, a retaining element of the subject disclosure may include any suitable number of engagement elements, such as 1, 2, 3, 4, 5, 6, 7, 10, or more. In such a manner, the degree of expansion of the implant may be controlled, at least in part, by the movement of the end member over the engagement element(s). Additionally, as depicted, the proximal end 54 of the retaining element 54 may include an abutment 55, configured herein as a raised ledge element.

Figure 2C:
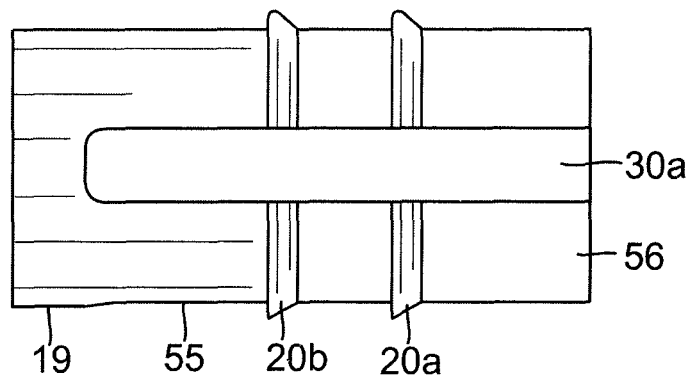
FIG. 2C illustrates an enlarged side view of the distal portion of the retaining element for the embodiment illustrated in FIGS. 2A and 2B.

As can be seen in particular with reference to FIG. 2C, the retaining element (19) additionally includes a deformation configuration (30), which deformation configuration is adapted for allowing the distal portion (55) of the retaining element (19) to deform, such as in response to a force, for instance a force applied to the expansible implant (10) for causing the implant to expand. It is to be noted that the engagement elements (20a,b) includes several ridge sections that are separated by a plurality of deformation configurations (30a, b, c), which deformation configurations are shaped as oval windows.

As depicted in reference to FIG. 2C, the distal portion 55 of the retaining element 19 may include a plurality of engagement elements (e.g., 20a-b, etc.) that are positioned at the distal portion 55 of the retaining element 19, and configured to allow the movement of an end member in one direction, e.g., the forward direction, such as toward an opposing end member, but to not allow the movement of the end member in the reverse direction, e.g., away from an opposing end member. As can be seen with reference to FIG. 2C, the distal portion 55 of the retaining element 30a may include a deformation configuration 30a, in this instance, configured as U-shaped cut-out, which deformation configuration is adapted for being deformed so as to facilitate the movement of an end member over a corresponding engagement element As can be seen with reference to FIG. 3A, the retaining member 19 may include a plurality of engagement elements (e.g., 20a-20b), wherein the engagement elements 20a-b are adapted for interacting with an end member (e.g., 3b) so as to keep the implant 10 from contracting once expanded. For example, the retaining element 19 includes a plurality of engagement elements (20a-20b) that are configured as raised ridges. The raised ridges may be sloped or curved on one portion and straight, or non-sloped on a second portion, such that the engagement element includes a surface that curves away from the retaining element and a surface that is substantially normal to the retaining element. The end member (e.g., 3b) may include a configuration 11 that is adapted to interact with the raised ridges of the engagement elements 20, such that as the configuration 11 passes forward over the raised ridge 20a, the end member 3b is prevented from moving backwards over the same engagement element 20a, due to the interaction of configuration 11 with the engagement element 20a. It is to be notes, that although as depicted in FIG. 3B-3C the end member 3b includes a special configuration 11 for interaction with the raised ridge member, such a configuration is not necessary as the end member itself may be configured as a whole or in part to interact with the raised ridge member so as to allow movement in a forward direction while preventing movement in a backward direction.

Figure 3A:
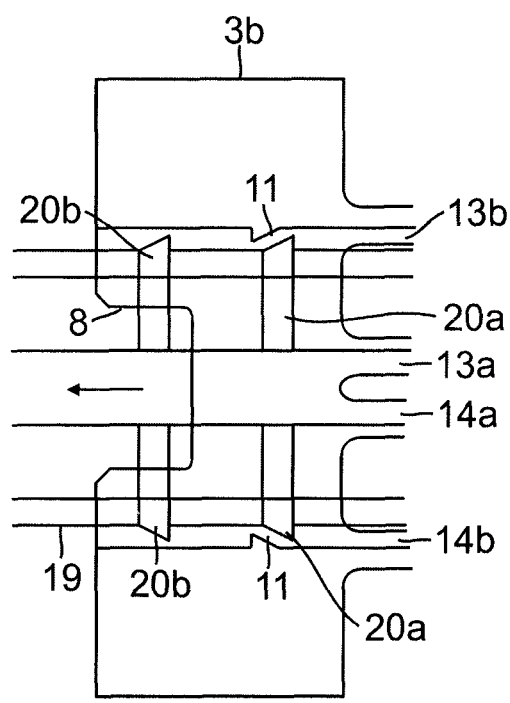
FIG. 3A illustrates the interaction of a retaining element with a portion of the end member of the implant of the disclosure prior to the retaining element being engaged by the end member.

FIG. 3A shows the interaction of the end member 3b with the raised ridge member 20a prior to the passage of the configuration 11 over the ridge member 20a, thus movement is permitted in the forward and or backward direction with respect to the end member 3b and engagement element 20a. FIG. 3B shows the interaction of the end member 3b with the raised ridge member 20a after the passage of the configuration 11 over the ridge member 20a, thus movement is now permitted only in the forward direction, with respect to the end member 3b and engagement element 20a, and movement is now prohibited in the reverse or backward direction.

It is to be noted that although the configuration 11 is shaped as an extend edge member, the configuration, if included, may have any suitable shape and may be of any suitable size so long as it is capable of interacting with an engagement element so as to allow movement of an end member along a retaining element in one direction, e.g., in a forward direction toward an opposing end member, and to prevent movement in a reverse or backward direction, e.g., in a direction away from an opposed end member. Accordingly, the end member may include an engagement element, such as configuration 11, wherein the engagement element may have any suitable shape and size, although, as depicted, configuration 11, includes an extended body that extends away from an interior surface of an aperture of the end member. In the illustrated embodiment, the configuration includes at least two surfaces, one that is sloped and/or curves away from the interior surface of the aperture of the end member, and one adjoining surface that is radiates substantially normal to the interior surface of the aperture of the end member and joins the curved surface at the apex of the curvature.

Figure 3B:
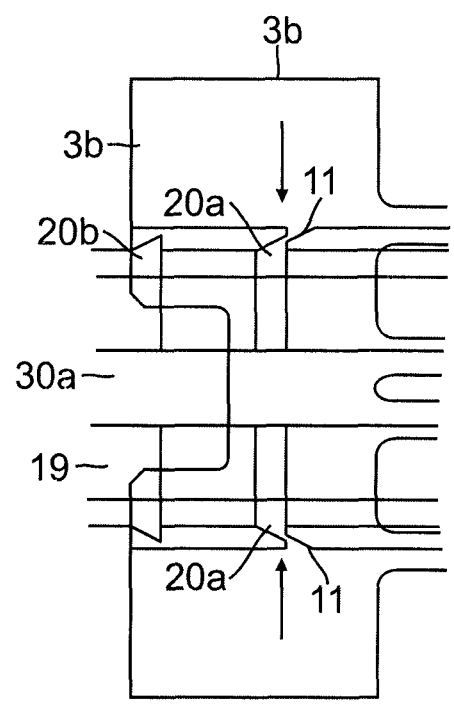
FIG. 3B illustrates the interaction of a retaining element with a portion of the end member of the implant of the disclosure after the retaining member has been engaged by the end member.

Accordingly, as depicted in FIG. 1B, and as can be seen in particular with reference to FIGS. 3A and 3B, the engagement element 20 of the retaining element 19 and the end member 3b are configured for interacting with each other in such a manner that as the implant 10 is expanded, at least a portion of the end member 3b is associated with the engagement element 20, so as to prevent the implant 10 from contracting once expanded. For instance, as depicted in FIGS. 3A and 3B, as the end member (3b) moves along the extended retaining element (19) toward the opposed end member (3a), and the implant (10) is expanded, the end member (3b) contacts and/or passes over one of the engagement element (20) and is thus prevented from moving horizontally away from the opposed end member (3a). In this manner, the engagement element (20) is adapted for retaining the implant (10) in the expanded configuration.

Figure 4A:
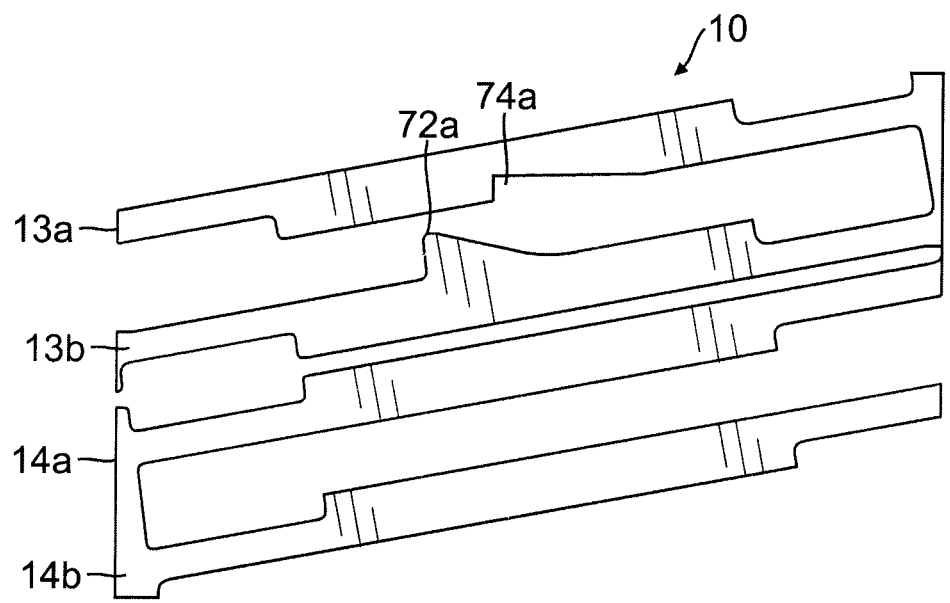
FIG. 4A illustrates a side view of a pair of first and second supports of an implant of the disclosure, wherein the supports include an engagement element depicted prior to expansion of the implant.
Figure 4B:
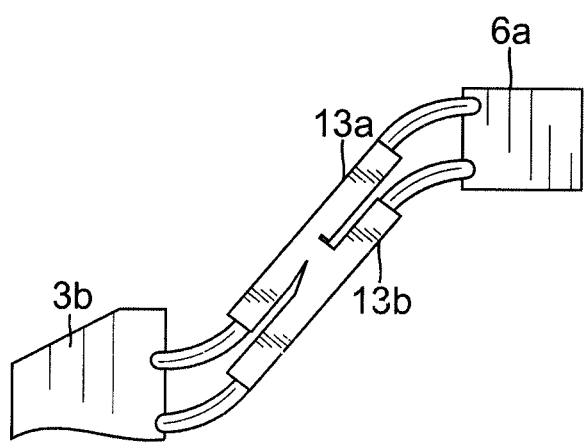
FIG. 4B illustrates a side view of the pair of first and second supports of FIG. 4A, wherein the are depicted after the expansion of the implant.

As can be seen with reference to FIGS. 4A and 4B, in certain embodiments, the mechanical resistance may be an engagement element 72 and an engagement element (e.g., receiving member) 74. For instance, as depicted, the expansible implant 10 may include at least a pair of first and second supports, e.g., 13a and 13b, that are associated with at least one of a first and/or second plate(s), e.g., 6a, and additionally associated with at least one of a first and/or second end member(s), e.g. 3b, as described above. As depicted, one of the pair of the first and second supports, e.g., 13b, includes an engagement element, and the other of the first and second supports, e.g., 13a, includes an engagement element receiving member. The engagement element 72a and the receiving member 72b are configured for associating with one another in such a manner so as to restrain the implant 10 from contracting once expanded.

For instance, as can be seen with respect to FIG. 4A, the implant 10, includes a plurality of pairs of first and second supports (13a,b and 14a,b). The first and second supports 13a,b include engagement element receiving element 74a and engagement element 72a, respectively. First and second supports 14a and 14b do not include either of an engagement element receiving element or an engagement element. The implant 10 is in a collapsed or folded configuration and the first and second supports 13a and 13b are capable of moving in respect to one another, thus, the implant 10 is capable of being expanded. However, as illustrated in FIG. 4B, as the implant 10 is expanded, first and second supports 13a and 13b move relative to one another in such a manner that the engagement element 72a is contacted and becomes engaged with the receiving member 74a, such that once expanded, the implant 10 is prevented from contracting or otherwise collapsing due to the coupling of the engagement element receiving member's association with the engagement element of the first and second supports 13a and 13b, respectfully. It is to be noted, that although the engagement element 72a is configured as a tooth element and the receiving member 74a is configured as a notch element, these configurations may differ in any suitable fashion, as described above, so long as they are capable of interacting in a corresponding fashion so as to prevent the movement of the first and second supports relative to one another and thereby are capable of preventing the contraction of the implant once expanded.

An expansion element, e.g., implant expander, for causing the opening out of the expansible implant may also be included. As can be seen with reference to FIGS. 5A and 5B, the implant expander 110 may be a tubular element with an extended body 120. The extended body 120 may include a proximal portion 122 with a proximal end 124, and a distal portion 126 with a distal end 128. The proximal portion 122 may include a proximal end 124, wherein the proximal end 124 is configured for being coupled to, or otherwise associated with, an end member, e.g., 3b and/or a retaining element 19 of an expansible implant 10.

Figure 5A:
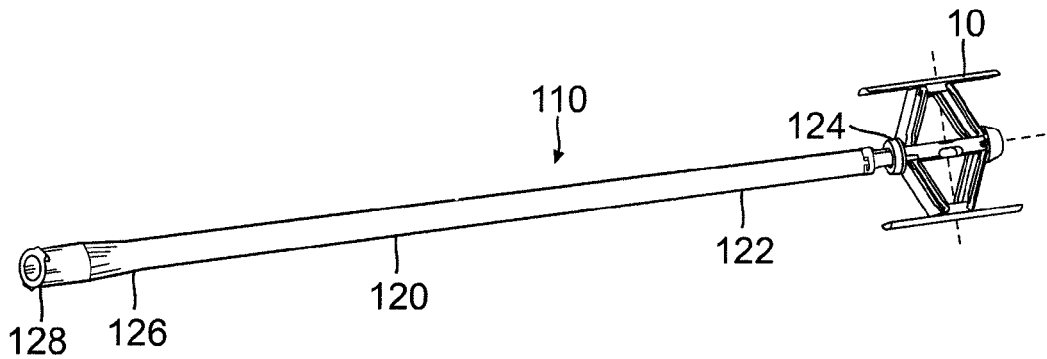
FIG. 5A illustrates a perspective view of an implant expander in association with an implant in accordance with the disclosure, wherein the implant is in expanded configuration.
Figure 5B:
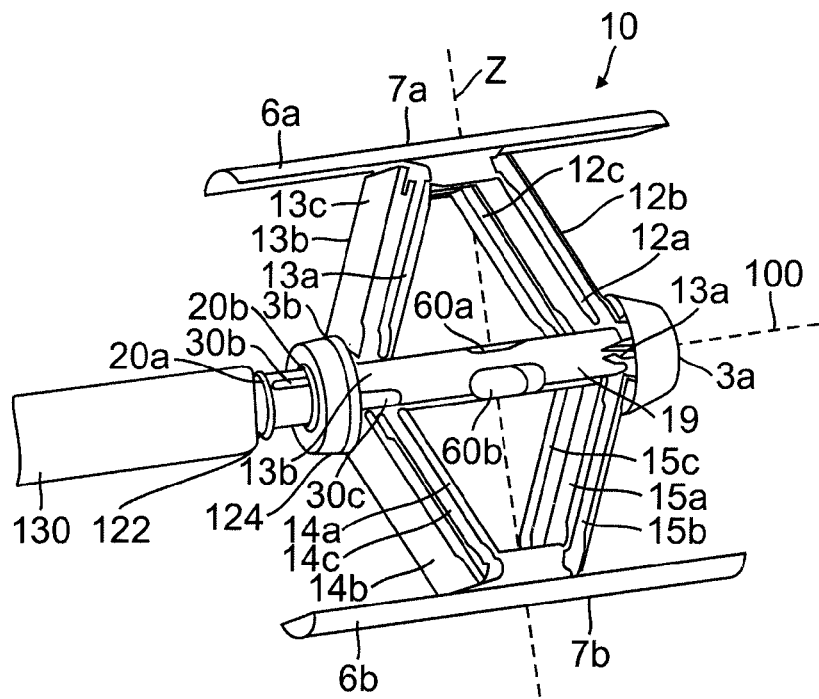
FIG. 5B illustrates an enlarged view of the association of the implant expander with the implant as presented in FIG. 5A.

As can be seen with reference to FIG. 5B, an expansible implant 10 is provided in association with an implant expander 110. The expansible implant 10 includes end members 3a and 3b, opposed plates 6a and 6b, with bearing surfaces 7a and 7b, as well as retaining element 19. The implant is expandable in an expansion plane 2, and includes support members 12 and 13 of upper plate 6a and the corresponding symmetrical support members 14 and 15 on the lower plate 6b, allowing opening out of the plates. It is noted that support members 12, 13, 14, and 15 each include 3 support arms a, b, and c, respectively. Accordingly, a support member, e.g., 12, 13, etc. may include 1, 2, 3, 4, or any suitable number of support arms.

The retaining element 19 may be used to allow one or more of the end members 3a and 3b of the implant 10 to be brought together when placed in an implant position between two restoration surfaces, such as between two bone surfaces, and to restrain the implant 10 in the expanded configuration once expanded. For instance, a retaining element 19 may be included where the retaining element includes a proximal and distal ends as well as an elongate portion there between. The retaining element 19 may have moveably associated therewith a moveable end member, e.g., 3b, such that as when the end member, e.g., 3b, is engaged, for instance, by a proximal end 124 of an implant expander 110, the end member 3b of the implant 10 may be moved along the retaining element 19 and brought toward an opposing end member, e.g., 3a. As depicted, the retaining element 19 may additionally include one or more engagement elements 20a,b, such as raised ridge portions, e.g., positioned on one or more of its distal portions, which engagement elements 20a,b are configured for interacting with the end member, e.g. 3b, or a portion thereof, so as to prevent the implant 10 from collapsing once it has been expanded.

Specifically, the engagement elements, e.g., 20a,b, may be configured such that as the implant expander 110 engages the end member, e.g., 3b, and effectuates the movement of the end member, e.g., 3b, longitudinally along the retaining element 19 toward the opposing end member, e.g., 3a, the end member, e.g., 3b, traverses the engagement elements, e.g., 20a, and is thereby prevented from moving backwards back across engagement element, e.g., 20a, and away from the opposed end member, e.g., 3a. In this manner, the presence of the one or more engagement elements ensure movement of the one or more end members toward one another and prevent substantial movement of the end members away from one another. Thus, the implant 10 is configured such that it can be expanded, e.g., by the implant expander 110, but once expanded it is prevented from collapsing.

Additionally, the engagement elements, e.g., 20a,b, of the retaining element 19, when engaged in association with the expansion of the implant, may also allow the implant to be expanded to a desired expansion—i.e., if a plurality of engagement elements members are included and positioned along the retaining element, the number and positioning of the individual engagement elements of the retaining element may correspond to a predetermined height of the expanded implant. Additionally, a control configuration may be provided by the supports and articulations associated therewith, wherein the thickness of the material webs defining the articulations are capable of deforming in the plastic region so as to allow the expansion of the plates of the implant to substantially preserve a determined opening-up position of the plates, apart from elastic shrinkage which is negligible in practice.

The expansion of the plates 6a and 6b of the implant, and their stabilization once opened up, can be achieved through adaptation of the bearing surfaces 7a and 7b in plates 6a and 6b, respectively, to the bone and/or space geometry. Further, in some embodiments of the disclosure, the implant 10 allows a non-parallel displacement of plates 6a and 6b and, at the end of the displacement, allows a definitive position of the plates in a non-parallel state if necessary (e.g., as a function of the bone anatomy). For example, the expansion of plates 6a and 6b may be non-parallel if the lengths of individual supports (e.g., 12 and/or 13, etc.) are of different lengths. For example, if supports 12 and 14 are longer than supports 13 and 15, opening out the implant will force plates 6a and 6b to angle away from each other. In FIGS. 1A-2B, this would result that plates 6a and 6b at end 3b to be further apart from one another then at end 3a. As one of ordinary skill in the art will appreciate, depending upon the configuration, only one respective support need be lengthened/shortened, to obtain a particular angle. It is worth noting, that plates 6a and 6b may be symmetrical with respect to a plane which is substantially perpendicular to the plane of expansion 2 passing through the longitudinal axis 100 of the implant 10 in order to obtain, during the expansion of the implant, the displacement of the two plates in a manner parallel to the longitudinal axis 10.

It is to be noted, that in the implant expanders 110 association with the end member, e.g., 3b, the proximal end 124 of the implant expander 110 may have a configuration that is complimentary to at least a portion of the end member, e.g., 3b. In this manner, the proximal portion 124 of the implant expander 110 is configured for being removeably associated with the end member, e.g., 3b, and may be used to exert a force thereon, which force may effectuate the movement of the end member, e.g., 3b, along the retaining element 19, across engagement elements 20a,b, and toward opposing end member, e.g., 3a. Because the end members 3a,b are coupled to supports 12 and 13, respectively, and because the supports 12 and 13 are associated with plate 6a, the movement of the end member 3b toward the end member 3a causes the supports 12 and 13 to move radially away from the central axis 100, which in turn pushes the plate 6a away from the central axis 100. The same is true for the corresponding elements for plate 6b. In this manner, as the implant expander 110 engages end member 3b and effectuates the movement of the end member in the forward direction toward the opposing end member 3a, the opposed plates 6a and 6b are pushed away from one another and the implant is expanded. As indicated above, the presence of suitable engagement elements, e.g., 20a,b, prevent the implant from collapsing once expanded.

An additional feature of the implant expander 110 and implant 10 is that they may also be configured for facilitating the delivery of a fluid, such as a bone cement, to a cavity wherein the implant is positioned. For instance, the retaining element 19 may be extended, tubular, and may include a passage there through as well as egress apertures, e.g., 60a,b. The extended body of the retaining element 19 includes a proximal and a distal end, wherein the distal end may be configured for being coupled to a fluid injector 130. The fluid injector 130 may be a part of the implant expander 110 or may be a separate element that is fitted within a passageway of the implant expander 140. The fluid injector 130 and/or implant expander 110 may be coupled to a suitable pumping mechanism and/or to a fluid reservoir. In this manner, fluid, e.g., bone cement, may be passed from the fluid reservoir through the fluid injector 130, to the passage of the retaining element 19, and out of the egress aperture(s) 60a,b so as to be delivered to the cavity within which the implant 10 is positioned.

Figure 6A:
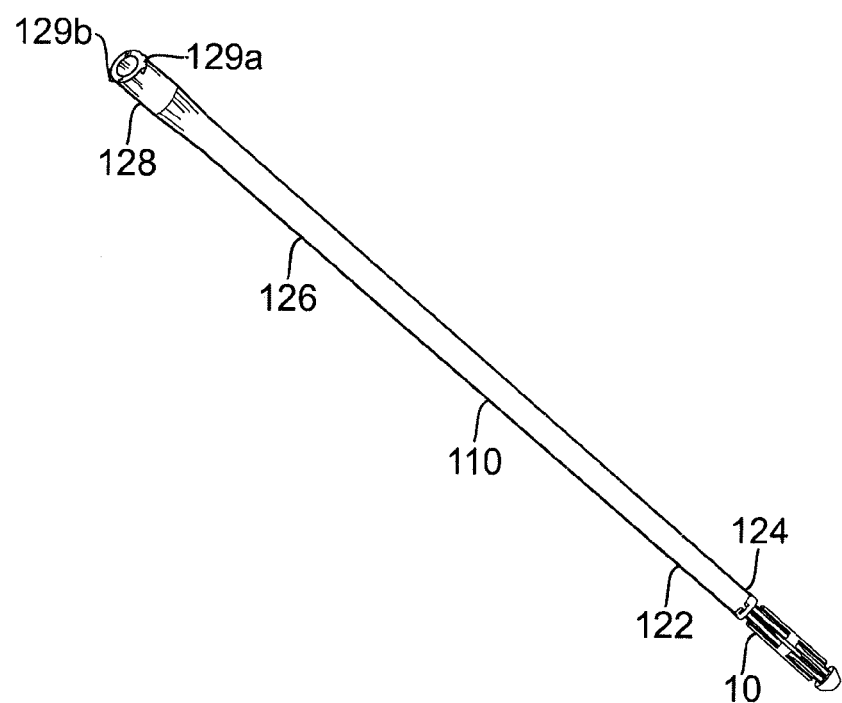
FIG. 6A illustrates an side view of a distal end of an implant expander in association with an implant.
Figure 6B:
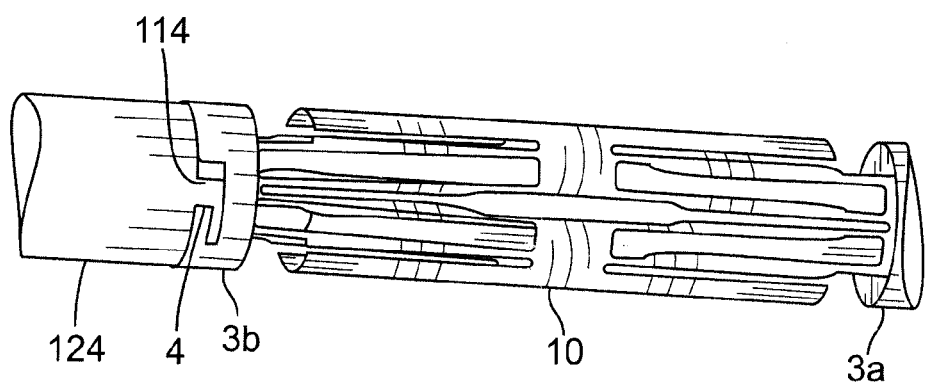
FIG. 6B illustrates a perspective view of the implant expander and implant of FIG. 6A, wherein the implant expander is shown in full.
Figure 6C:
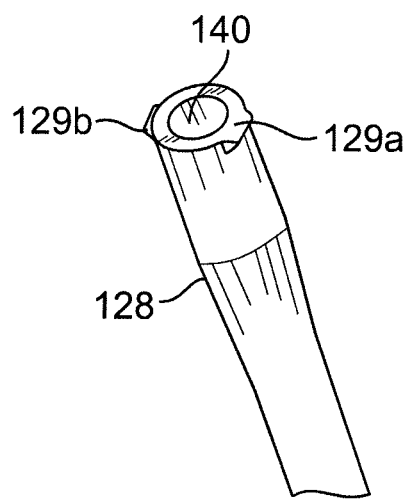
FIG. 6C illustrates an side view of a proximal end of the implant expander set forth in FIG. 6B.

As can be seen with respect to FIGS. 6A-6C, the implant expander 110 may be coupled to an implant 10 at a distal end 124 of a distal portion 122 of the implant expander 110. For instance, as can be seen with respect to FIG. 6C, the implant expander may include one or more protruding ledge member(s) 114 that is adapted to fit within a cut-out receiving member 4 of the end member 3b so as to allow the implant extender 110 to be removably coupled and/or otherwise affixed to the implant 10. As can be seen with reference to FIG. 6C, the implant expander may additionally include a configuration on a proximal end 128 of a proximal portion 126 of the implant expander 110, wherein the configuration is adapted for allowing the implant expander 110 to be coupled to a fluid injection system. For instance, a proximal portion 126 of the implant expander 110 may have a raised surface, relative to the distal portion 122, and may include wing members 129a,b that are adapted for allowing the proximal end 128 of the implant expander 110 to be coupled to an injection assembly. In certain embodiments, the configuration may be a luer lock configuration.

At least some of the disclosed implant embodiments, as briefly noted earlier in the disclosure, may be used in methods of using or methods of treatment, for the alleviation of back pain and/or the restoration and/or treatment of adverse spinal conditions. For instance, the implant may be inserted between two vertebrae, for example, to retain or expand a spacing there between, or the implant may be inserted within a vertebral body, for example, to retain or expand the space therein.

Figure 7:
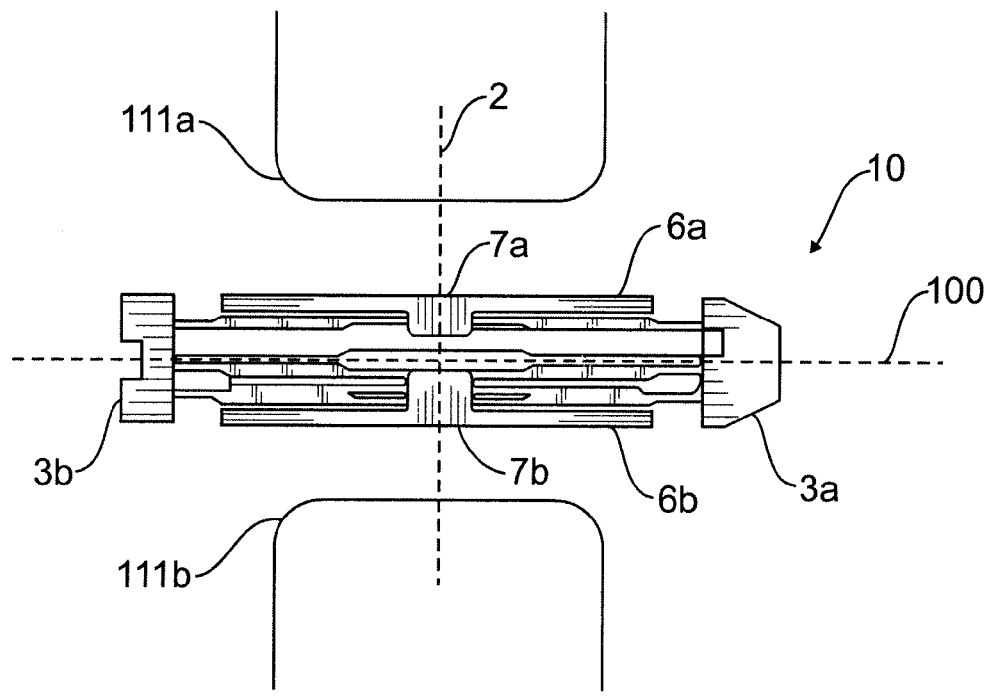
FIG. 7 illustrates a lateral view of the implant of FIG. 1A, as it would be post deployment between two surfaces/portions but pre-expansion.
Figure 8:
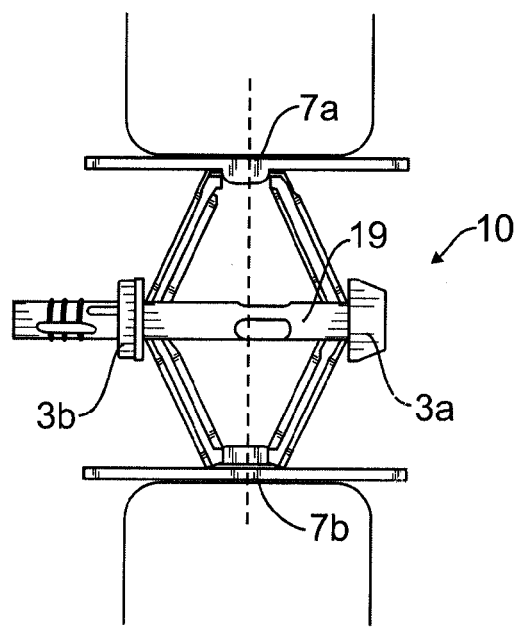
FIG. 8 illustrates a lateral view of the implant of FIG. 7, as it would be post deployment between two surfaces and post-expansion.
Figure 9:
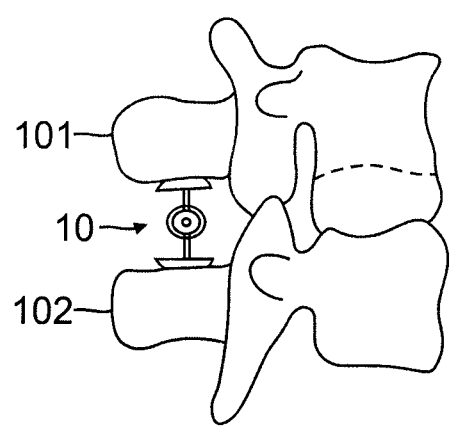
FIG. 9 illustrates a side view of the implant of FIG. 7, as it would be post deployment between two surfaces and post-expansion.
Figure 10:
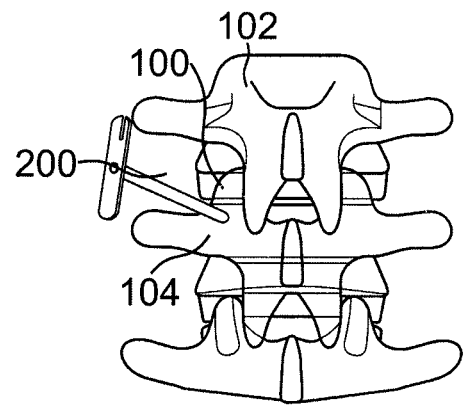

FIGS. 7-9 illustrate an expansible implant of the subject disclosure as it would be employed as an intervertebral implant between two vertebrae where one or more of the vertebrae and/or the space between the vertebrae needs to be retained or restored. It is to be understood, however, that although FIGS. 7-9, and the related disclosure, are directed to the use of an expandable intervertebral implant, as disclosed herein, for the retention or expansion of a space between two vertebrae, the devices and methods disclosed herein are equally applicable to the use of an expandable intravertebral implant, as disclosed above, for the retention and/or expansion of the space within a vertebral body. As such, the following disclosure and FIGS. 7-9 are not meant to be limiting in any way in this regard, and the methods are equally applicable except that the implant will be configured for insertion into a space within a vertebral body and the method steps modified accordingly. Together FIGS. 7-9 illustrate steps of a general method for restoring a portion of a spinal column. For instance, as illustrated in FIG. 7, the method involves the step of inserting (e.g., percutaneously) an expansible implant 10 according to some embodiments, in a collapsed configuration between two vertebrae, e.g., between adjacent spinous processes.

Specifically, in some embodiments, the method includes the implant being inserted and positioned in such a manner that the bearing surfaces 7a and 7b, and/or recesses (if included), of the plates 6a and 6b align with a portion of a vertebrae 111a and 111b in a plane of expansion 2a (for example), such that as the implant 10 is expanded plates 6a and 6b move outwardly from a central axis 100, in the plane of expansion 2a, the recesses 8a and 8b engage the corresponding vertebrae portions 111a and 111b.

As illustrated in FIG. 8, once inserted and positioned between the bone portions, the end member 3b and/or retaining element 19 of the expansible implant 10 may be engaged and the implant expanded so that the bearing surfaces 7a and 7b engage the associated bone portions 111a and 111b, respectively. The presence of retaining members 20a,b, ensure that the implant will not collapse once expanded. FIG. 9 illustrates a fully expanded expansible implant once it has been deployed between the two portions of two adjacent bones 101 and 102, for instance, adjacent spinous processes.

A general method for restoring a portion of a spinal column using an implant will now be described. Specifically, the method involves inserting, e.g., percutaneously, an expansible implant 10 into a body, wherein the implant is in a collapsed configuration. See FIG. 1. The implant may be inserted, for instance, between two surfaces, e.g., intervertebral bone surfaces, in need of restoration, such as between adjacent spinous processes.

For example, the expansible implant of the disclosure may be deployed as an intervertebral implant between two different vertebral bones wherein one or more the bones themselves and/or the space between the bones needs to be restored. The method may involve the step of inserting (e.g., percutaneously) an expansible implant 10 of the subject disclosure in a collapsed configuration into a body, for instance, between two bones, e.g., bone portions, in need of restoration, such as between adjacent spinous processes 111a and 111b. For example, in a percutaneous approach, a sharp instrument may be inserted between the two spinal processes into the interspinous ligament, performing a hole which will accept the insertion of the implant.

In some embodiments, the method includes the implant 10 being inserted between two opposing bone portions 111a and 111b and positioned in such a manner that the bearing surfaces 7a and 7b of the plates 6a and 6b align with the associated bone portions 111a and 111b. For instance, the implant may be inserted in a symmetrical way along the sagital plane.

Once inserted and positioned, the implant may be rotated clockwise or counterclockwise by any amount, e.g., by about 45° to about 135°, for instance, about 90°, so that the implant 10 is in an expansion position. For example, a position wherein the bearing surfaces 7a and 7b of the plates 6a and 6b are both aligned and in plane with a portion of the bone portions 111a and 111b along plane 2a, such that as the implant 10 is expanded plates 6a and 6b move outwardly from a central axis 100, in the plane of expansion 2a, and the bearing surfaces 7a and 7b engage the bone portions 111a and 111b. The implant may be rotated by any suitable means, for instance, via the rotation of an implant expander associated therewith. See FIG. 6A.

For instance, in some embodiments, the implant may be held in place in association with an implant expander, whereby the implant expander maybe rotated thereby rotating the implant. For example, the implant expander or the part of the implant expander where the implant is associated (see FIG. 6B) may be rotated. In this manner, the implant may easily be inserted through an opening created in a body and rotated into correct orientation so as to be aligned with a suitable plane of expansion without causing substantial stress on the bones, e.g., spinal process.

Further, in some embodiments, the rotating allows for the implant to have a good, e.g., tight fit, between the implant, e.g., bearing surface, and the bone portion, e.g., spinal process, in contact therewith. In some embodiments, the implant may be larger in one direction than another. Thus, the implant may be inserted with the small height in the direction of the expansion. The higher height may therefore be positioned into the transversal plane. Hence, by rotating the implant the higher height is positioned into the direction of expansion. The bearing surface 7a,b may then come into place, for instance, in contact with the spinous bone. In this manner, for example, the implant may be introduced between the spinous processes and placed between the vertebrae prior to expansion, without constraining the spine.

Once rotated so that plates 6a and 6b are aligned in plane 2a between two bone portions, e.g., spinous processes, the implant expander 110 may effectuate the expansion of the implant via its association with the end member 3b and/or retaining element 19, such that when the end member is engaged by the implant expander 110, the end member 3b is traversed over engagement elements 20a,b, and moved horizontally along the retaining element 19 toward opposing end member 3a and the implant is expanded, as illustrated in FIG. 5B. For instance, once inserted, rotated (if necessary), and positioned between two bones in need of restoration, the end member 3b and/or retaining element 19 of the expansible implant 10 is engaged and the implant is expanded so that the bearing surfaces 7a and 7b engage bone portions 111a and 111b.

Methods of using at least some of the disclosed embodiments, such as those described briefly above, enable the alleviation of back pain and/or the restoration and/or treatment of adverse spinal conditions. For instance, according to some embodiments, the implant is used in an intervertebral application, where the implant may be configured so as to be inserted into an intervertebral space between two vertebrae (for example), or inserted between two bone segments of vertebrae (e.g., two adjacent vertebrae). For instance, in some embodiments, such as where there has been a deterioration of the intervertebral disc, an intervertebral implant according to some embodiments may be inserted, in a collapsed configuration into the deteriorated region between two vertebrae and, once appropriately positioned, may be expanded so as to restore or retain the space between the two vertebrae. In some embodiments, the implant is inserted between two spinous processes of adjacent (for example) vertebrae. In some embodiments, the implant is used in an intravertebral application, such as a vertebroplasty procedure, where the implant may be configured so as to be inserted into an intravertebral space within a vertebral body (for example). For example, in some embodiments, such as where there has been a spinal fracture, such as that caused by osteoporosis, an intravertebral implant according to some embodiments of the disclosure, may be inserted, in a collapsed configuration into the deteriorated region within a vertebral body and, once appropriately positioned, may be expanded so as to restore or retain the space within the vertebral body.

Accordingly, in some embodiments, a method for restoring a space, for instance the space between two vertebrae or the space between two opposed cortical bones within a vertebra, is provided. The method may include one or more of the following steps. For example, the method may include accessing the space, inserting an implantable expandable device of the disclosure therein, e.g., in a collapsed configuration, positioning the expandable device between two surfaces within the space, and expanding the device so as to restore the space. The step of accessing the step may include one or more of surgically creating an entry through the tissue of a patient, inserting a trocar there through, associating a pin with the trocar, sliding an awl over the pin, applying a drill and/or tube guide, e.g., wire, over the pin, shaping the space via employment of the drill, insert an implant gauge to prepare the space, associate the implant with the implant holder and insert the implant and holder through the trocar to the site of delivery, and expanding the implant along a plane of expansion. One, two, or more expandable implants may be delivered in this manner. Once the one or more implants have been delivered and expanded, the implant holder may be removed and an injection tube may be inserted through the trocar, and cement may be injected into the space. The injection tube and/or trocar may be removed along with any other instrumentation and the access may be closed using routine surgical procedures.

For instance, an expansible implant of the disclosure may be indicated for the treatment of vertebral body fractures, such as those due to traumatism or osteoporosis. The following is provided an exemplary procedure for such an indication. For example, a patient may be positioned in such a manner so as to reduce any load on the fractured vertebra(e). Specifically, the patient may be placed in a hyper-lordosis position, for example, when a lumbar fracture is indicated.

An implant of the disclosure may be implanted using any approach known in the art. For instance, the implant may be inserted by a transpedicular and/or a percutaneous approach. Access to the vertebral body may be achieved via the pedicles. Such an approach typically requires a minimum pedicle diameter thereby allowing the insertion of a drill, such as a drill with a diameter of 5.4 mm.

A knowledge of the delivery site is useful and may be obtained in any sufficient manner as known in the art, such as by an MRI scanner or other imaging methodology. Once the specific dimensions of the delivery site, and/or surrounding bone portions, have been determined, an expansible implant with the appropriate dimensions for implantation into the delivery site may be selected. For instance, in certain embodiments, the implant should have a size that is adapted to the size of the vertebral body (or vertebral bodies) to be treated. For example, in some embodiments, the size may be around 0.5 mm, L25 mm. One, two, or more implants can be used for restoring the space. Accordingly, when evaluating the delivery site, the number of implants to be delivered can be determined, for example, according to the size and to the geometry of the fracture, which in turn may depend on a determined fracture geometry and/or vertebra size.

An exemplary procedure for the implantation of an expansible implant of the disclosure will now be described with reference to FIGS. 10 to 19. In one method, the dimensions of the delivery site are determined, an access angle and path are selected, and as seen with reference to FIG. 10, a trocar 200 is positioned, e.g., under fluoroscopic imaging, so as to enter the pedicle 100 between vertebrae 102 and 104 along a frontal plane.

Figure 11:
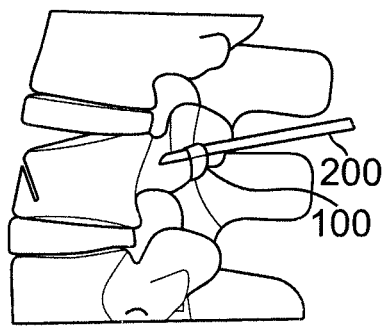

In an alternative embodiment, as illustrated in FIG. 11, the trocar 200 may be positioned relative to the pedicle 100 along a sagital plane. The trocar 100 may be driven into the tissue and/or bone so as to achieve an appropriate position, such as, for example, approximately within the first third of the vertebral body, so as to fix the axis for the remaining steps of the procedure. The use of an imaging device, such as X-ray imaging, may be used so as to ensure appropriate positioning of the trocar, e.g., along the frontal or sagital plane.

Figure 12:
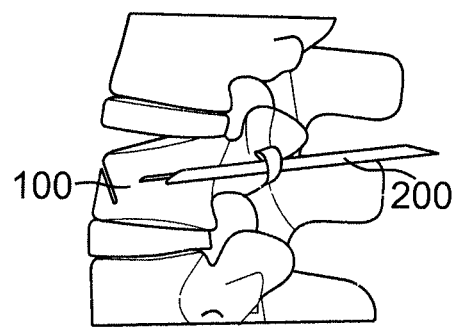
Figure 13:
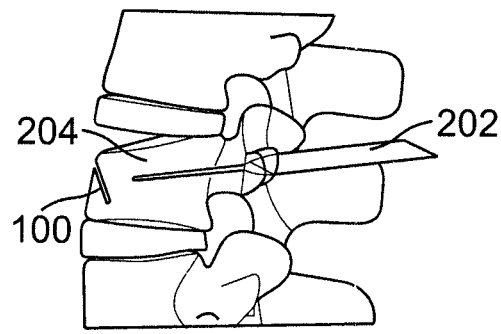

As can be seen with respect to FIG. 12, the stylus of the trocar 200 may be replaced by a pin 202, which pin 202 may be fixed to the medium of the vertebra body 100 and the trocar may then be removed. The use of an imaging device, such as X-ray imaging, may be used so as to ensure appropriate positioning and fixing of the pin, e.g., along the frontal or sagital plane. As illustrated in FIG. 13, once the pin 202 has been appropriately positioned, an awl, such as a square awl 204, may be positioned and slid over the pin 202 in a manner sufficient to puncture the cortical part of the pedicle so as to facilitate the insertion of a drill. A protection sleeve may then be positioned, if desired, so as to facilitate delivery of a tube guide.

Figure 14:
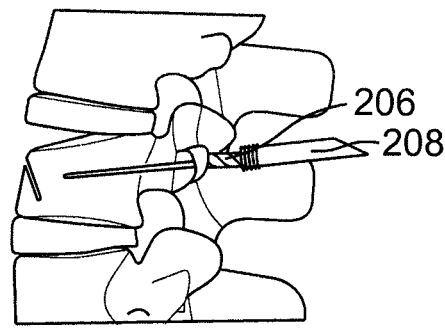
Figure 15:
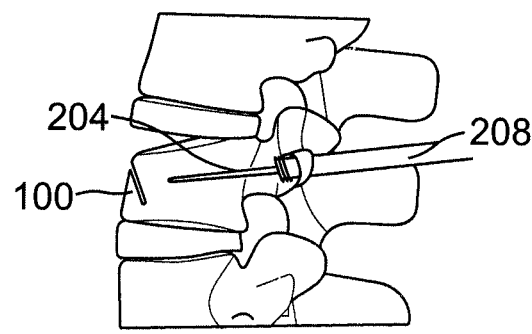
Figure 16:
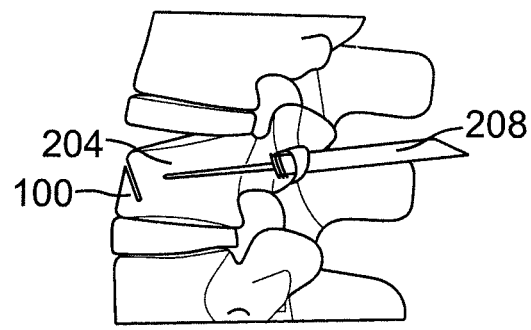
FIG. 16 illustrates a side view of a vertebra with a tube guide inserted there through and associated with the vertebra.

As can be seen with respect to FIG. 14, a drill 206 may be assembled and positioned at the delivery site. For instance, the drill 206 may be assembled in part applying a brake washer and tube guide 208 thereto and the entire assembly may be positioned over the pin. For example, the positioning of the drill 206 may be such that it allows the tube guide 208 intermediate guidance compared to the pin. The use of an imaging device, such as X-ray imaging, may be used so as to ensure appropriate positioning of the drill and/or tube guide, e.g., along the frontal or sagital plane. Such imaging may be important so as to prevent rupture of the pedicle. As illustrated in FIG. 15, the tube guide 208 may be positioned so as to be inserted into the pedicle proximal cortical and affixed thereto, for instance, by screwing. For example, the tube guide may include 1, 2, 3, or more threads, such as at 120°, which allow the tube guide 208 to be stabilized within the pedicle. Specifically, in some embodiments, the tube guide may be inserted through the soft tissue by applying a counterclockwise force thereto, however, the fixing thereof to the bone may be via clockwise motion (e.g., clockwise screwing). Once the tube guide 208 has been fixed into the pedicle proximal cortical, the pin may be removed, e.g., before drilling, as illustrated in FIG. 16.

Figure 17:
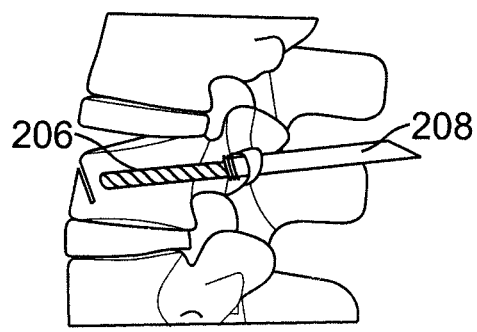
Figure 18:
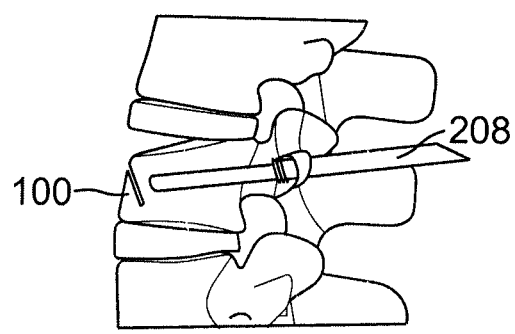
FIG. 18 depicts the vertebra of FIG. 17 with the drill removed.

Once the drill 206 has been appropriately positioned, as illustrated in FIG. 17, both the pedicle and the vertebra body 100 may be drilled in such a manner so as to produce a space with optimal dimensions for implant delivery, positioning, and/or expansion. For example, once the appropriate drilling depth has been achieved and validated, the brake washer may be positioned against the tube guide, graduation of the brake washer on the drill may be determined, and reproduced on an implant gauge on an implant of the disclosure. Once the vertebra body 100 has been drilled, the drill may be removed, as illustrated in FIG. 18. If desired, a probe can be used to check the access and/or delivery site.

Figure 19:
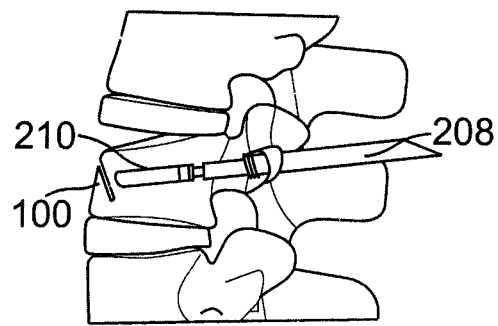
Figure 20:
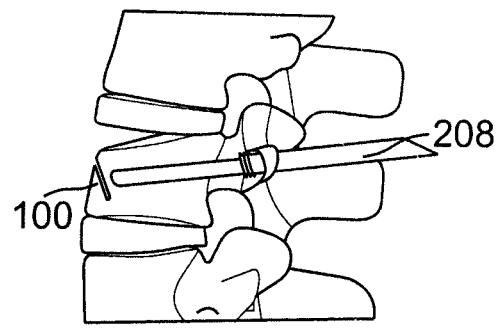
FIG. 20 depicts the vertebra of FIG. 19 with the implant gauge removed.

An implant gauge 210 may be inserted into the prepared access as illustrated in FIG. 19. For instance, the brake washer may be positioned on the implant gauge in a manner similar to that as described above with respect to the drill, e.g., with the same or similar graduation as before located on the drill. For example, the graduation indicated on the drill by the brake washer may be reproduced on the implant holder. The implant gauge 210 may be inserted into the access so as to prepare the implant site. For instance, adjustment of the depth can be effectuated so as to ensure optimal positioning of the implant. The implant gauge 210 may then be removed as illustrated in FIG. 20. A probe may be used to assess the configuration of the access and/or implant bed, e.g., space, prior to insertion of the implant.

Figure 21:
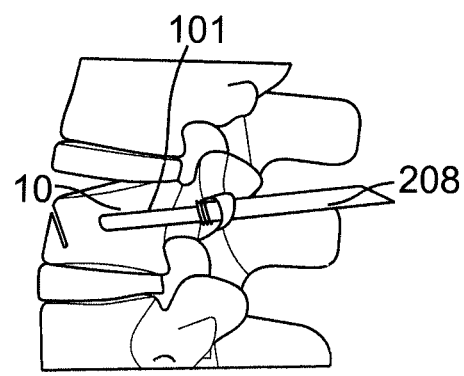
Figure 22:
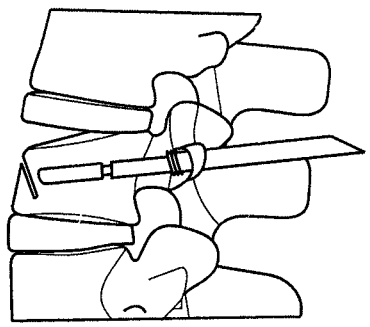
FIG. 22 illustrates a vertebra with an implant inserted therein.

FIG. 21 illustrates the insertion of the implant holder 101 and/or implant 10. For instance, the brake washer may be positioned on the implant holder 101 and the graduation determined from the implant gauge may be reproduced. The implant 10 is affixed to the implant holder 101 and the affixed assembly is inserted into and through the access hole prepared by the drill, for instance, until the brake washer is stopped by the tube guide. As illustrated in FIG. 22, the implant 10 may then be adjusted, for example, in a manner so that its plane of expansion is parallel to the vertebra mechanical axis, e.g., the implant expansion may be parallel to the implant holder handle.

Figure 23A:
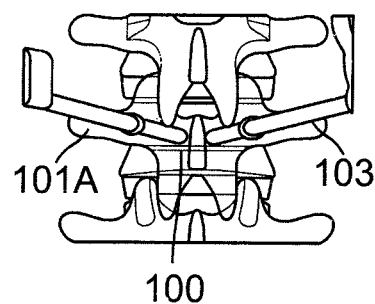
FIG. 23 depicts the vertebra of FIG. 10 with an additional access there through, which additional access includes a trocar there through and the original access includes a cannula plug.
Figure 23B:
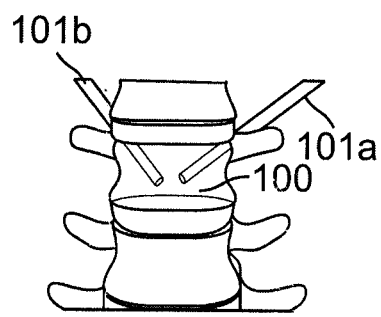
Figure 24:
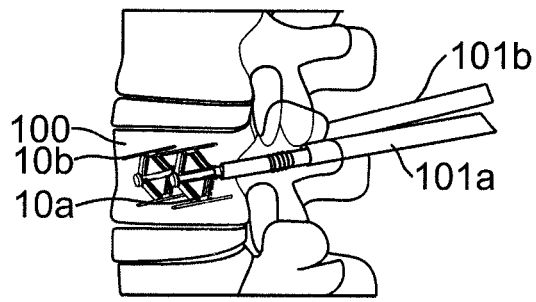
FIG. 24 depicts the vertebra of FIG. 23 with two implants inserted therein along with two implant holders.
Figure 25:
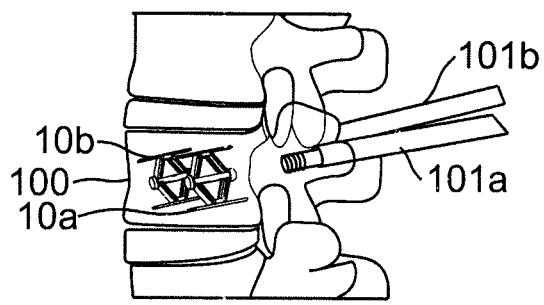
FIG. 25 depicts the vertebra of FIG. 24 with two implants inserted therein and the two implant holders removed.

As illustrated in FIGS. 23-25, one or more of the above steps may be repeated for the implantation of one or more additional expansible devices of the disclosure, for instance, by insertion through a second pedicle. As illustrated in FIGS. 23A and B, a second pedicle in vertebra 100 may be accessed for delivery and implantation of a second expandable device. A forward view of the vertebra 100 with one implant holders 101a and a cannula plug 103 inserted into vertebra 100 through two different pedicle access points is depicted in FIG. 23A. FIG. 23B depicts a rearward view of the vertebra 100 of FIG. 23B, with two implant holders 101a and 101b inserted into the vertebra 100. FIG. 24 depicts a side profile view of the vertebra 100 of FIG. 23B. As depicted, implant holders 101a and b include expandable implants 10a and b. As can be seen with reference to FIG. 24, once inserted and appropriately positioned within the vertebra 100, the implants 10a and 10b may be expanded, e.g., progressively and/or alternatively, for instance, by screwing the expansion handle of the implant holder 101 in order to reduce the fracture. It is noted that the implants may also be expanded at the same time, if desired. The reduction of the fracture may be imaged, by methods well known in the art, such as by X-ray imaging or fluoroscopic monitoring. After the desired expansion has been achieved, the implant holder(s) may release the implant(s), e.g., by unscrewing the expansion handle, from the implant and the implant holder(s) may be removed as illustrated in FIG. 25.

Figure 26:
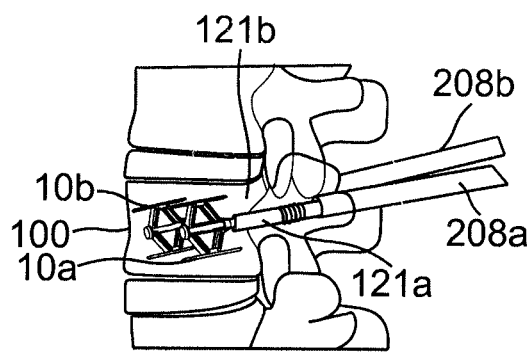
FIG. 26 depicts the vertebra of FIG. 25 with two implants and two injection tubes inserted therein.
Figure 27:
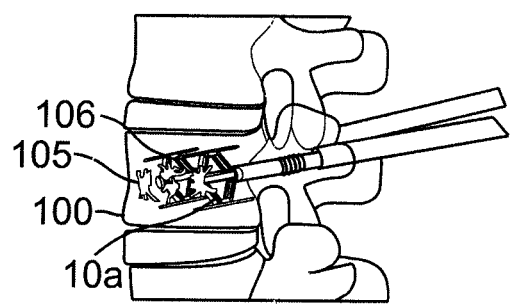
FIG. 27 depicts the vertebra of FIG. 26 with two implants inserted therein and two injection tubes inserted therein, wherein a filling material is being inserted through the injection tubes.
Figure 28:
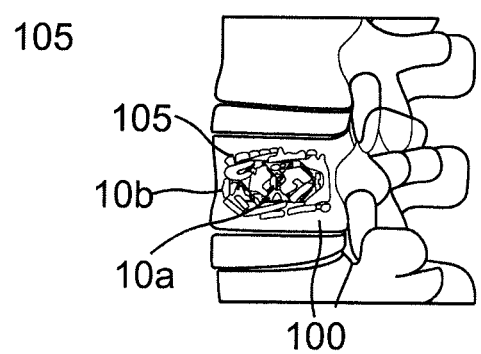
FIG. 28 depicts the vertebra of FIG. 27 with two implants inserted therein and the two injection tubes removed.

If desired, a filler material may be delivered to the prepared space as depicted in FIGS. 26-28. For instance, as illustrated in FIG. 26 an injection tube 121a and b may be inserted through the access via the tube guide 208a and b, respectively, and into the vertebra space, for example, until the tip of the injection tube 121a and b reaches the implant 10a and b, respectively. The positioning of the injection tube may be determined by fluoroscopic imaging. Once appropriately positioned, as illustrated in FIG. 27, a filler material, such as a bone cement 105, may be injected into the vertebra space to fill the implant and surrounding bone structures. The filling process may be monitored, for instance, by fluoroscopic monitoring, so as to determine the appropriate amount of filling. Once the appropriate amount of filling has been achieved the injection tube 121a and b and tube guide 208a and b may be removed, as illustrated in FIG. 28, and the access closed in accordance with routine surgical procedures well practiced in the art.

Figure 29A:
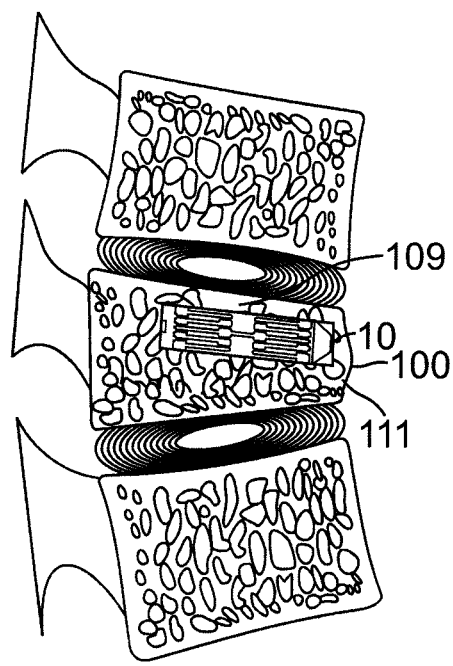
FIG. 29A illustrates a vertebra with a device of the disclosure inserted therein, wherein the device is in a collapsed configuration.
Figure 29B:
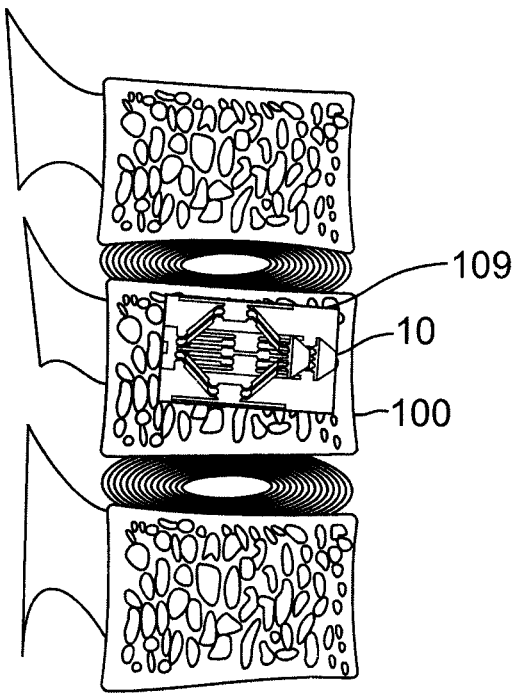
FIG. 29B illustrates a vertebra with a device of the disclosure inserted therein, wherein the device is in an expanded configuration.

FIG. 29A illustrates in greater detail an exemplary embodiment of implanting an expansible implant of the disclosure in accordance with the methods described herein. As depicted, the implant 10 has been inserted into a prepared space within a vertebra 100. The implant 10 is in a collapsed configuration and is positioned close to the upper cortical endplate 109. For example, in some embodiments, 1 to 5, such as 2 to 4, including 3 mm of space, e.g., spongy bone material, may be left between the implant 10 and the endplate 109, so that the upper plate of the implant 10 may push against the vertebral endplate 109 upon expansion, as shown in FIG. 29B. Additionally, as illustrated the implant 10 is positioned close to the anterior wall 111 of the vertebra 100. For instance, in certain embodiments, the implant 10 may be positioned such that there is 1 to 8, such as 2 to 6, including 3 to 5 mm of space, e.g., spongy bone material, left between the implant 10 and the anterior wall 111. It is to be noted, that as the implant 10 expands, as illustrated in FIG. 29B, this distance may increase, e.g., in certain embodiments the implants length may decrease from about 1 mm or less to about 8 mm or more, such as about 2 mm to about 6 mm, for instance, about 3 mm to about 5 mm, including a decrease in length of about 4 mm. The implant 10 should be positioned so as not to pierce the anterior wall 111. The position of the implant 10 may be determined prior to expansion, for instance, via imaging techniques well known in the art, so as to ensure the implant is fully inside the vertebral body, e.g., is not in the pedicle.

Figure 30A:
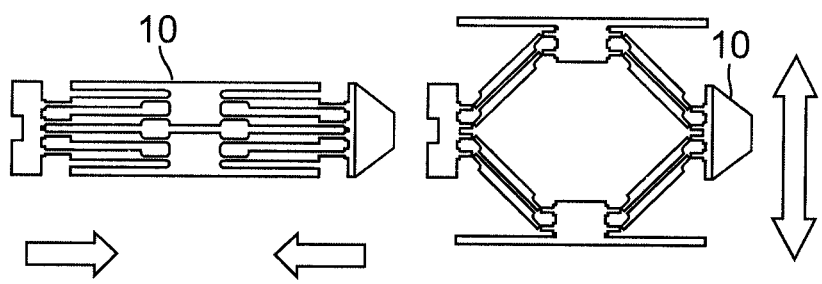
FIGS. 30A and 30B illustrate a device of the disclosure in a collapsed and expanded configuration.
Figure 30B:
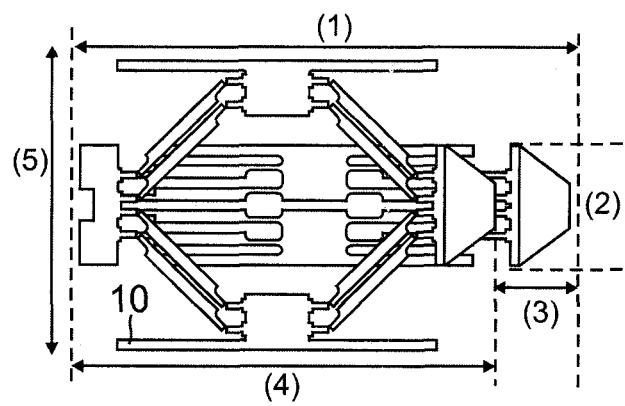

FIGS. 30A and B illustrate the implant 10 in a collapsed configuration and an expanded configuration. FIG. 30B illustrates exemplary configurations with associated dimensions of the implant 10 as it moves from a collapsed configuration to an expanded configuration. As depicted (1) represents the initial length of the implant 10 when inserted in a collapsed configuration. The initial insertion length may be of any appropriate length given the space into which the implant is to be inserted, but typically will range from about 15 mm to about 30 mm, such as about 20 mm to about 25 mm. (2) represents the initial diameter of the implant upon initial insertion. The initial insertion diameter may be of any appropriate diameter given the space into which the implant is to be inserted, but typically will range from about 1 mm to about 10 mm, such as about 3 mm to about 7 mm, including about 5 mm. (3) represents the decrease in length of the implant 10 as it moves from the collapsed configuration to the expanded configuration. The decrease in length may be of any appropriate length given the desired expansion of the implant and the space into which the implant is to be inserted and expanded, but typically will range from about 1 mm to about 8 mm, such as about 3 mm to about 5 mm, including about 4 mm. Accordingly, (4) represents the length of the implant 10 after maximal expansion. The length of the implant 10 after maximal expansion may very dependent on the configurations described above, but may generally be about 10 mm to about 30 mm, such as about 15 mm to about 25 mm, including about 20 mm. (5) represents the maximal expansion of the implant 10. The maximal expansion of the implant 10 may very dependent on the configurations described above, but may generally be about 10 mm to about 30 mm, such as about 15 mm to about 25 mm, including about 20 mm.

Figure 31:
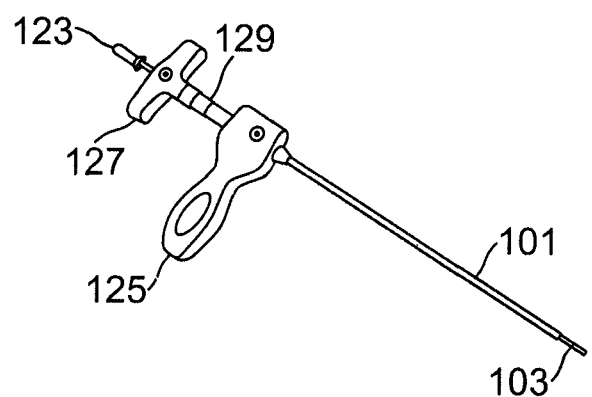
FIG. 31 illustrates an implant holder in accordance with the disclosure.
Figure 32:
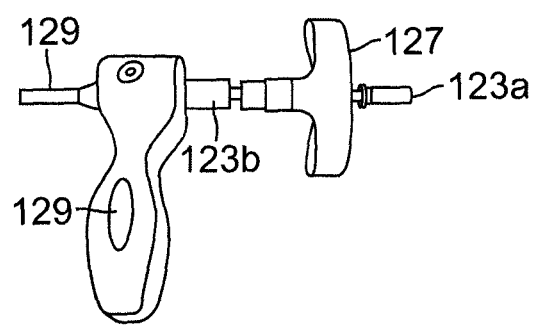
FIG. 32 illustrates a proximal portion of the implant holder of FIG. 31.

FIGS. 31 to 34 illustrate an implant holder 101 and an implant 100 of the disclosure. FIG. 31 illustrates an implant holder 101. The implant holder includes a stem 121, a knob 123 of the stem, a holding handle 125, an expansion handle 127, and a cylinder 129, of the holding handle. FIG. 32 illustrates a closer viewpoint of a proximal portion of the implant holder 101. A holding handle 125, an expansion handle 127, a cylinder 129, and two portions of the knob of the stem 123a and b are depicted. As illustrated, the expansion handle 127 is free between the knob of the stem and cylinder 129, and in such a configuration an implant 10 may be associated with the implant holder 101.

Figure 33:
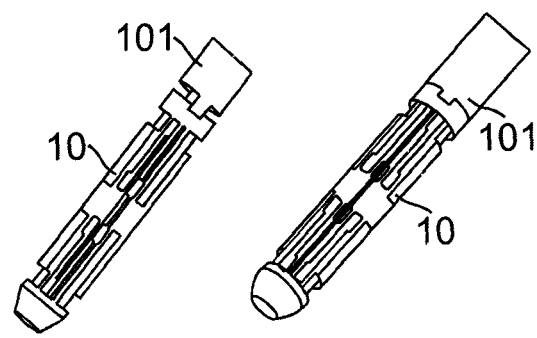
FIG. 33 illustrates a distal portion of an implant holder associates with an implant in accordance with the disclosure.

FIG. 33 illustrates the association of the implant 10 with the implant holder 101. As depicted, the implant 10 and implant holder 101 include corresponding threads such that the implant 10 may be screwed into the implant holder 101. Specifically, the stem of the implant holder 101 may inserted into the implant 10 as depicted at (1) along the axis of the implant. The distal end of the implant 10 is depicted at (2) and as illustrated, the end of the stem, depicted at (3) of the implant holder 101 comes to the distal end (2) of the implant 10, e.g., the screwed extremity of the stem (3) comes to the limit of the distal end (2) of the implant 10. For instance, the stem screwed extremity may be fixed on the distal end of the implant. The screwing may be performed, for example, up to pre-stressing of the implant and the stem should not exceed the implant.

Figure 34:
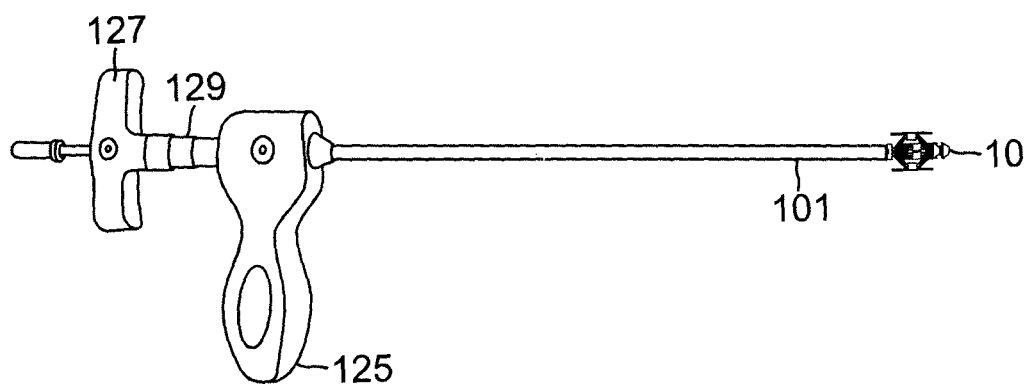
FIG. 34 illustrates an implant holder associated with an implant in accordance with the disclosure.

FIG. 34 illustrates the expansion of an implant 10 by the implant holder 101. As depicted, the plane of expansion for the implant is equivalent to the axis of the holding handle 125. Accordingly, the holding handle axis is equivalent to the implant expansion axis. As illustrated, the expansion handle 127 is in contact with the cylinder 129 of the holding handle 125 and the implant 10 has been expanded.

It will thus be seen that the disclosure attains the objects made apparent from the preceding description. Since certain changes may be made without departing from the scope of the present disclosure, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current disclosure.

While the disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the disclosure. All such modifications are intended to be within the scope of the claims appended hereto.

What is claimed is:
1. A vertebral expandable implant, comprising:
first and second bearing surfaces intended to evenly move away from one another according to a plane of expansion during expansion of the implant;
at least first and second opposed ends of the implant associated with each of the bearing surfaces; and
a retaining element for retaining the implant in an expanded configuration,
at least one support extending linearly between one of the at least first and second opposed ends of the implant and an underneath side of one of the first and second bearing surfaces, wherein:

the retaining element comprises a deformable portion, a first end associated with the first end of the implant and a second end associated with the second end of the implant, a first engagement element provided proximate the second end of the retaining element for engagement with a second engagement element provided on the second end of the implant, and engagement between the first and second engagement element and deformation of the deformable portion of the retaining element substantially prevents the second end of the implant from moving away from the first end of the implant.

2. The expandable implant according to claim 1, wherein the first engagement element comprises one or more protruding ridges that extend outward away from an outer surface of the retaining element, and wherein the second engagement element comprises one or more recesses that extend inward away from an outer surface of the end of the implant, wherein upon expansion of the implant, at least a portion of at least one of the ridges abuts a portion of and/or is received by at least a portion of one or more recesses.

3. The expandable implant according to claim 2, wherein the one or more ridges at least partially circumscribe the outer surface of the retaining element.

4. The expandable implant according to claim 3, wherein the one or more ridges completely circumscribes a circumference of the outer surface of the retaining element.

5. The expandable implant according to claim 1, wherein the one or more deformation portions is configured as a circle, triangle, square, rectangle, oval, u-shape, or oblong.

6. The expandable implant according to claim 1, wherein the second engagement element comprises one or more protruding ridges that extend outward away from an outer surface of the end of the implant, and wherein the first engagement element comprises one or more recesses that extend inward away from an outer surface of the retaining element, wherein upon expansion of the implant, at least a portion of at least one of the ridges abuts a portion of and/or is received by at least a portion of one or more recesses.

7. The expandable implant according to claim 6, wherein the retaining element is tubular and the one or more recesses at least partially circumscribe the outer surface of the retaining element.

8. The expandable implant according to claim 6, wherein the one or more recesses comprise notches.

9. The expandable implant according to claim 1, wherein the retaining element is tubular and comprises a lumen configured for allowing the passage of a flowable material there through.

10. The expandable implant according to claim 9, wherein the retaining element further comprises an aperture configured for allowing the egress of the flowable material from the lumen of the tubular retaining element.

11. The expandable implant according to claim 1, wherein at least one of the ends of the implant is configured for association with an implant expander.

12. The expandable implant according to claim 11, wherein the implant expander comprises a proximal portion and a distal portion, wherein the distal portion is configured for association with at least one of the ends of the implant.

13. The expandable implant according to claim 12, wherein the proximal portion of the implant expander is configured for being coupled to an injection member of an injection system.

14. The expandable implant according to claim 13, wherein the proximal portion comprises a luer lock, threaded, or bayonet configuration.

15. The expandable implant according to claim 1, wherein expansion of the implant comprises movement of at least one of the ends of the implant relative to the retaining element.

16. The expandable implant according to claim 10, wherein the material comprises a mixture.

17. The expandable implant of claim 16, wherein the material comprises a bone cement or bone graft.

18. An expandable implant, comprising:
a first and second bearing surfaces, wherein the first and second surfaces are intended to evenly move away from one another according to plane of expansion during expansion of the implant;
at least first and second opposed end members associated with each of the bearing surfaces;
a retaining element; and
at least a pair of supports associated with at least one of the bearing surfaces, at least one of the bearing surfaces additionally associated with at least one of the end members, wherein
a first support of the pair including a first engagement element, said first support extending linearly between one of the at least first and second end members and an underneath side of one of the first and second bearing surfaces upon expansion of the implant,
a second support of the pair including a second engagement element, said second support extending linearly between the one of the at least first and second end members and the underneath side of the one of the first and second bearing surfaces upon expansion of the implant, and
upon expanding the implant a predetermined amount, at least a portion of the first engagement element engages with at least a portion of the second engagement element to prevent movement.

19. The expandable implant according to claim 18, wherein the first engagement element comprises one or more protruding ridges that extend outward away from an outer surface of the retaining element, and wherein the second engagement element comprises one or more recesses that extend inward away from an outer surface of the end of the implant, wherein upon expansion of the implant, at least a portion of at least one of the ridges abuts a portion of and/or is received by at least a portion of one or more recesses.

20. The expandable implant according to claim 19, wherein the one or more ridges comprise teeth and the one or more recesses comprise notches.

21. The expandable implant according to claim 19, wherein at least one of the first and second bearing surfaces correspond to a respective plate.

22. The expandable implant according to claim 18, wherein the retaining element is tubular and includes a lumen configured for allowing the passage of a material there through.

23. The expandable implant according to claim 18, wherein the retaining element further comprises an aperture configured for allowing the egress of the material from the lumen of the tubular retaining element.

24. A method for restoring a space between two surfaces, comprising the steps of:
inserting an expandable implant, wherein the expandable implant includes a contracted and an expanded configuration, and the implant comprises:
a first and second opposed plates each including a recess configured for engaging a portion of a respective vertebrae of two vertebrae adjacent each respective plate, wherein the first and second plates are intended to move away from one another according to a plane of expansion as the implant is expanded;

at least first and second opposed end members associated with each of the opposed plates, wherein at least one of the end members includes an aperture configured for receiving one end of a retaining element;

a retaining element; and at least a pair of first and second supports associated with at least one of the first and second plates and additionally associated with at least one of the first and second end members, wherein at least one of the pair of the first and second supports comprises a first engagement element and a second engagement element for engagement with the first engagement element;

aligning the recesses with respective vertebral bones such that when the implant is expanded the recesses engage a portion of the vertebral bones; and expanding the implant from the contracted configuration to the expanded configuration and thereby restoring the space.

25. The method according to claim 24, wherein at least one of the first and second supports of the expandable implant comprises the engagement element and another of the first and second supports comprises the engagement element receiving member, additionally wherein the engagement element and the receiving member are configured for associating with one another in such a manner so as to restrain the implant from contracting once expanded.

26. The method according to claim 24, wherein the engagement element is configured as a tooth element and the receiving member is configured as a notch element.

27. The method according to claim 24, wherein expansion of the implant comprises movement of at least one of the end members relative to the retaining element.

28. The method according to claim 24, comprising a plurality of engagement elements and a plurality of engagement element receiving members.

29. The method according to claim 24, wherein the retaining element retains the implant in the expanded configuration.

30. The method according to claim 24, wherein positioning further includes rotating the implant so as to align the recesses with the vertebral bones.

31. The method according to claim 24, wherein the implant is inserted in a collapsed configuration.

32. The method according to claim 24, wherein the space comprises a space between two separate vertebrae and the surfaces comprise a surface on two opposed vertebral bones.

33. The method according to claim 24, wherein the space comprises a space within a vertebral body and the surfaces comprise opposed surfaces within the vertebral body.

34. An expandable implant, comprising:

a first and second bearing surfaces, wherein:
  the first and the second bearing surfaces remain substantially parallel to each other during expansion of the implant, and
  the first and second surfaces are intended to evenly move away from one another according to plane of expansion during expansion of the implant;

at least first and second opposed end members associated with each of the bearing surfaces;

a retaining element; and at least a pair of supports associated with at least one of the bearing surfaces, at least one of the bearing surfaces additionally associated with at least one of the end members, wherein
  a first support of the pair including a first engagement element,
  a second support of the pair including a second engagement element, and
  upon expanding the implant a predetermined amount, at least a portion of the first engagement element engages with at least a portion of the second engagement element to prevent movement.

35. The expandable implant according to claim 34, wherein the first engagement element comprises one or more protruding ridges that extend outward away from an outer surface of the retaining element, and wherein the second engagement element comprises one or more recesses that extend inward away from an outer surface of the end of the implant, wherein upon expansion of the implant, at least a portion of at least one of the ridges abuts a portion of and/or is received by at least a portion of one or more recesses.

36. The expandable implant according to claim 35, wherein the one or more ridges comprise teeth and the one or more recesses comprise notches.

37. The expandable implant according to claim 35, wherein at least one of the first and second bearing surfaces correspond to a respective plate.

38. The expandable implant according to claim 34, wherein the retaining element is tubular and includes a lumen configured for allowing the passage of a material there through.

39. The expandable implant according to claim 34, wherein the retaining element further comprises an aperture configured for allowing the egress of the material from the lumen of the tubular retaining element.

40. The expandable implant according to claim 34, wherein the pair of supports are configured in a parallel arrangement.

* * * * *